United States Patent [19]
Moriwaki et al.

[11] Patent Number: 5,350,538
[45] Date of Patent: Sep. 27, 1994

[54] NOVEL HIGH POLYMER, FERROELECTRIC LIQUID-CRYSTALLINE COMPOSITION CONTAINING THE HIGH POLYMER AND RAW MATERIAL OF THE HIGH POLYMER

[75] Inventors: Fumio Moriwaki; Hiroyuki Endo; Satoshi Hachiya, all of Sodegaura, Japan

[73] Assignee: Idemitsu Kosan Co., Ltd., Tokyo, Japan

[21] Appl. No.: 85,093

[22] Filed: Jul. 2, 1993

[30] Foreign Application Priority Data

Jul. 8, 1992 [JP] Japan .................................. 4-203173

[51] Int. Cl.$^5$ ...................... C09K 19/52; C09K 19/12; C08G 77/04; C07F 7/04
[52] U.S. Cl. .................. 252/299.01; 252/299.65; 528/32; 528/33; 528/34; 528/43; 556/457; 556/465
[58] Field of Search ...................... 252/299.01, 299.65; 556/457, 465; 528/32, 33, 34, 43

[56] References Cited

U.S. PATENT DOCUMENTS

| | | | |
|---|---|---|---|
| 5,138,010 | 8/1992 | Keller et al. | 528/26 |
| 5,200,108 | 4/1993 | Yuasa et al. | 252/299.01 |
| 5,252,695 | 10/1993 | Niciri et al. | 252/299.01 |
| 5,259,987 | 11/1993 | McArdle et al. | 252/299.01 |

*Primary Examiner*—Sheam Wu
*Attorney, Agent, or Firm*—Antonelli, Terry, Stout & Kraus

[57] ABSTRACT

This invention provides a high polymer having the following repeating unit (I), a diene compound which is represented by the following formula (II) and is a raw material of the high polymer:

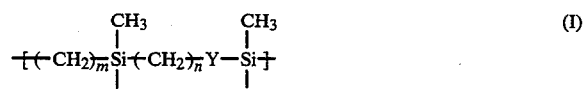

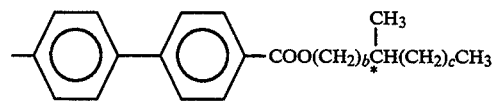

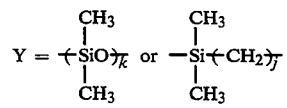

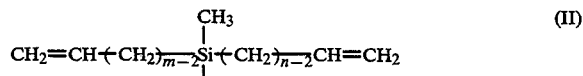

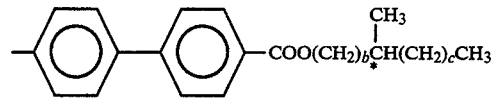

and a ferroelectric liquid-crystalline composition containing the high polymer and a low molecular weight smectic liquid-crystalline compound. The ferroelectric liquid-crystalline composition is easy to orient and exhibits a fast response against applied electric field.

18 Claims, 16 Drawing Sheets

NOVEL HIGH POLYMER, FERROELECTRIC LIQUID-CRYSTALLINE COMPOSITION CONTAINING THE HIGH POLYMER AND RAW MATERIAL OF THE HIGH POLYMER

BACKGROUND OF THE INVENTION (a) Field of the Invention

The present invention relates to a novel high polymer, a ferroelectric liquid-crystalline composition containing the high polymer and a raw material of the high polymer, more particularly, to a novel high polymer and a ferroelectric liquid-crystalline composition containing the same, which is useful in the field of optoelectronics, for example, as an element of liquid crystal devices which are incorporated into digital display devices of desk calculators and watches and clocks, dot-matrix display devices, electronic optical shutters, electronic optical diaphragms, optical modulators, optical-path transfer switches in optical communication systems, memory storages, liquid crystal printer heads and varifocal lenses.

(b) Description of the Related Art

Display devices produced by using low molecular weight liquid-crystalline compounds have been widely used, for example, for the digital display of desk calculators, watches and clocks. In these application fields, the conventional low molecular weight liquid-crystalline compounds generally are disposed between two glass substrates which are spaced out in the order of microns. In the production of large screens or curved screens, such an adjustment of the space, however, has been impossible.

To solve the problem, It has been attempted to develop polymeric liquid crystals, which are moldable in themselves [e.g., J. Polym. Sci., Polym. Lett., Ed. 13, 243(1975), Polym. Bull. 6, 309(1982), Japanese Patent Application Kokai Koho (Laid-open) No. 56-21479]. These conventional polymeric liquid crystalline compounds, however, are disadvantageous in that they cannot exhibit liquid-crystalline properties at room temperature and require heating at a temperature not lower than their glass transition temperatures and lower than their clearing points to form liquid-crystalline mesophases.

Japanese Patent Application Kokai Koho (Laid-open) No. 63-99204 discloses the synthesis of polyacrylate Ferroelectric, polymeric liquid-crystalline compounds, which are reported to exhibit excellent properties as compared to the above-described polymeric liquid-crystalline compounds. Even these conventional side chain ferroelectric, polymeric liquid-crystalline compounds are not satisfactory in the response speed and operable temperature range.

Japanese Patent Application Kokai Koho (Laid-open) No. 63-254529 discloses polyether ferroelectric, polymeric liquid-crystalline compounds, which are prepared by polymerizing epoxy monomers having optically active groups [for example, polymeric liquid-crystalline compounds which have the repeating units represented by formula ( IV') and prepared by polymerizing the epoxy compound represented by Formula (IV), u in the formulas (IV) and (IV') being an integer of 1 to 30].

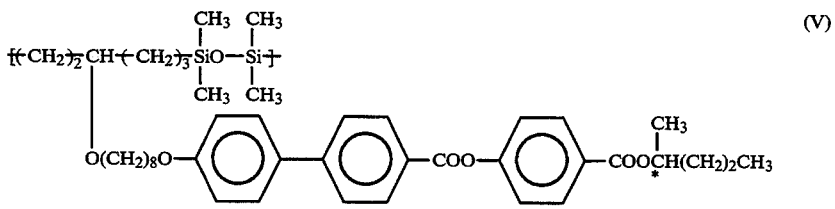

The pamphlet of International Publication No. 92/01731 discloses polymeric liquid-crystalline compounds which have repeating units whose side chains contain aromatic rings and whose main chains comprise a linear hydrocarbon structure and a siloxane structure, for example, the one represented by the following formula (V).

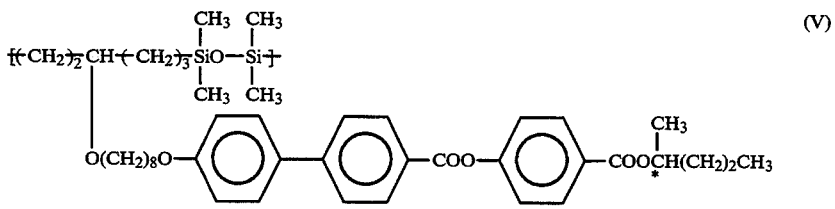

Although these conventional side chain ferroelectric, polymeric liquid-crystalline compounds have an advantage of responding against the stimulus of external electric field over a wide range of temperatures including room temperature, the response speed is still too slow for practical use.

There is a report of polymeric liquid-crystalline compositions which comprise low molecular weight liquid-crystalline compounds and polymeric liquid-crystalline compounds having asymmetric carbon atoms [Japanese Patent Application Kokai Koho (Laid-open) No. 63-284291]. However, the side chain polymeric liquid-crystalline compounds exemplified therein do not provide a sufficient space between side chains due to their conventional acrylate or siloxane main chains, and increasing their molecular weight disables the mixing of a large amount of low molecular weight liquid-crystalline compounds, making the speeding up of response speed difficult. This means that it is difficult to combine in such compositions a fast response and the advantages of high polymers.

As to the attempts of preparing compositions which have the merits of high polymers and as well exhibit a fast response by mixing non-liquid-crystalline, polymeric compounds and low molecular weight liquid-crystalline compounds, Japanese Patent Application Kokai Koho (Laid-open) No. 61-47427 discloses compositions which were endowed with an ability of self-form retaining by mixing low molecular weight liquid-crystalline compounds with non-liquid-crystalline high polymers. Since in these compositions, liquid crystal areas are dispersed in the matrix of the polymeric compounds (resins), there is a possibility that allowing the compositions to stand for a long time causes the separation of the low molecular weight liquid-crystalline compounds. Further, the compositions cannot exhibit sufficient contrast since the dispersed low molecular weight liquid-crystalline compounds form islands, and the dispersion system makes the control of orientation difficult. Japanese Patent Application Kokai Koho (Laid-open) Nos. 62-260859 and 62-260841 disclose ferroelectric composite film which contains low molecular weight liquid-crystalline compounds and thermoplastic resins which are compatible with the low molecular weight liquid-crystalline compounds. However, it is difficult to select low molecular weight liquid-crystalline compounds and thermoplastic resins which are compatible with each other, and the control of orientation is also difficult. There is another problem that the low molecular weight liquid-crystalline compounds should have ferroelectricity. Japanese Patent Application Kokai Koho (Laid-open) No. 1-198683 discloses compositions which comprise high polymers containing proton donors (or proton acceptors) and low molecular weight liquid-crystalline compounds containing proton acceptors (or proton donors). However, there is a problem that the structures of the high polymers and the low molecular weight liquid-crystalline compounds are considerably limited due to the essential condition that they should contain proton donors or proton acceptors.

SUMMARY OF THE INVENTION

An object of the present invention is to provide novel high polymers some of which form chiral smectic C phase at temperatures of a wide range including room temperature and respond at a high speed against the change of applied electric field.

Another object of the present invention is to provide diene compounds which are raw materials for the preparation of the novel high polymers.

Another object of the present invention is to provide ferroelectric liquid-crystalline compositions which comprise the high polymers and low molecular weight smectic liquid-crystalline compounds, are easy to orient and respond at a high speed against applied electric field.

Another object of the present invention is to provide ferroelectric liquid-crystalline compositions which comprise the high polymers, other high polymers and low molecular weight smectic liquid-crystalline compounds, are easy to orient and respond at a high speed against applied electric field.

As a result of investigation for accomplishing the objects described above, we found that a novel high polymer containing a specific mesogenic group in its side chains and a flexible siloxane chain in its main chain, having widely spaced side chains and further containing in its spacer a carbon-silicon bond, which is relatively free of restricted rotation, might be an excellent ferroelectric polymeric liquid-crystalline compound which forms chiral smectic C (S$_C$**  phase) at temperatures of a wide range including room temperature and responds at a high speed against the change of applied electric field. On the basis of this finding, we have completed the present invention.

That is, the present invention provides a novel high polymer comprising the repeating unit (I) represented by the following formula

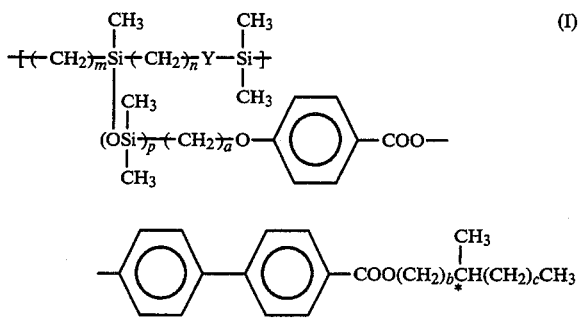

wherein each of m and n is an integer of 2 to 5, p is an integer of 1 or 2, a is an integer of 4 to 20, b is an integer of 0 to 3, c is an integer of 1 to 7, * represents an asymmetric carbon atom, and Y is

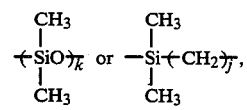

k being a number of 1 to 13 and j is an integer of 1 to 4.

Some of the high polymers of the present invention form S$_C$** and respond at a high speed against the change of applied electric field due to the flexible siloxane chain in their main chains, widely spaced side chains, and the carbon-silicon bond which is contained in the spacer and is relatively free of restricted rotation. Further, due to the wide space between the side chains, the high polymers are so compatible with low molecular weight liquid-crystalline compounds as to form a uniform mixture wherein phase separation does not occur. Therefore, whether the high polymers exhibit liquid-crystalline properties or not, they function as chiral dopants having excellent compatibility, and ferroelectric liquid-crystalline compositions easy to orient can be prepared by using the high polymers.

DESCRIPTION OF THE PREFERRED EMBODIMENTS

Figure 1:
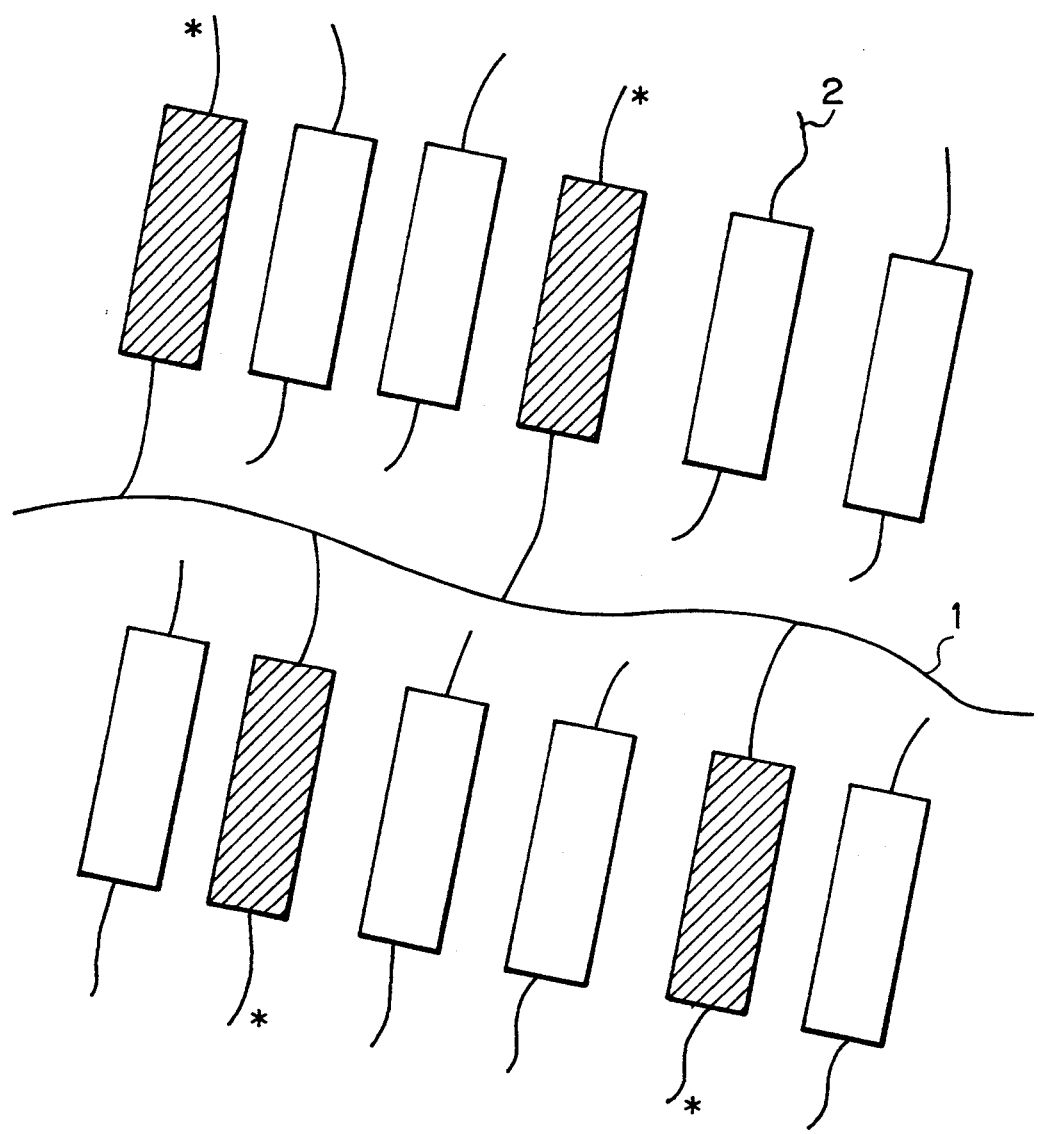
FIG. 1 is a schematic view illustrating the Ferroelectric liquid-crystalline composition of the present invention wherein a high polymer and a low molecular weight smectic liquid-crystalline compound are dissolved in each other to Form a uniform mixture.

The novel high polymer of the present invention generally has a weight average molecular weight (Mw) of 1,000 to 1,000,000, preferably 1,000 to 100,000. If Mw is less than 1,000, the high polymer may be difficult to form into film or coating, an Mw of more than 1,000,000 may make undesirable effects, such as an prolonged response time.

The high polymer of the present invention may be prepared by various methods which are not particularly limited, and, for example, it may be suitably prepared by copolymerizing a diene compound (compound II) represented by the following formula (II) and a silicon compound (compound VI) represented by the following formula (VI) in a predetermined ratio, in a solvent, in the presence of a catalyst, through a hydrosilylation.

chloroplatinate (IV), platinum (II) acetylacetonate and dicyclopentadienylplatinum chloride.

In the copolymerization, there is no particular limitation in the order and way of adding the above-described components. For example, it is preferable to add a solvent, such as toluene or THF, to the compound II, and then add thereto a predetermined amount of the compound VI and a catalytically sufficient amount of a catalyst, such as hydrogen hexachloroplatinate (IV). The catalyst may be added individually or in a form of a solution in a solvent, such as isopropyl alcohol.

The copolymerization may be carried out suitably in an atmosphere of an inert gas, such as gaseous nitrogen or argon, at, In general, a temperature of 60° to 120° C., preferably 80° to 100° C. The reaction time is generally about 3 to 30 hours.

Thus the objective high polymer can be synthesized. The high polymer obtained thus may be purified to a desired degree by separating and collecting it from the reaction mixture by means of known methods. In order to obtain a high polymer with a high purity, for example, it is preferable to carry out a purification by filtering the reaction mixture after the completion of the polymerization, followed by the removal of the solvent from the filtrate by distillation, the dissolution of the residue in a solvent, such as methylene chloride, and the purification of the solution by a column chromatography using a filler, such as silica gel.

Hereinafter, the compound II and the compound VI,

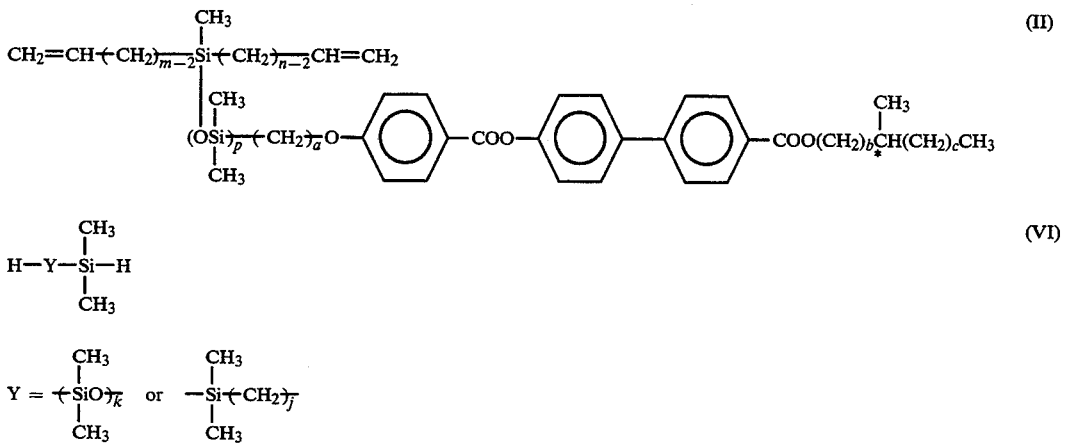

wherein, p, m, n, a, b, c, *, j and k are a defined above.

In the copolymerization, the ratio of the compound II to the compound VI may be selected depending on the desired polymerization degree of the high polymer. That is, a molar ratio (compound II/compound VI ) closer to 1 results in a high polymer of a higher polymerization degree, and a molar ratio larger or smaller than 1 results in a high polymer of a lower polymerization degree.

Preferred examples of the solvent to be used in the copolymerization of the compound II and the compound VI include inert aromatic hydrocarbons, such as benzene, toluene and xylene, inert ether, such as tetrahydrofuran (THF) and diisopropyl ether. The solvent to be used may be a single solvent or a solvent mixture, and, from the view point of the polymerization temperature, it is generally preferable to use a solvent laving a boiling point of 70° C. or higher. The catalyst to be used bas an hydrosilylating activity, and preferred examples include platinum catalysts, such as hydrogen hexawhich are the raw materials to be suitably used for the preparation of the high polymer of the present invention, will be described in detail.

Synthesis-I of the compound II

Step (1)

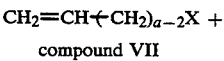

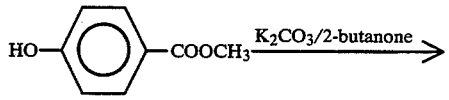

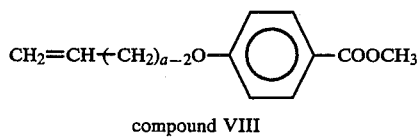

compound VIII

The etherification of a compound VII with methyl p-hydroxybenzoate is carried out in a solvent in the presence of a base, to obtain an etherified ester compound (compound VIII). The methyl p-hydroxybenzoate, which is used in step (1) for the reaction with the compound VII, may be replaced by other p-hydroxybenzoate than the methyl ester. The etherification in step (1) may be suitably carried out by mixing the compound VII, methyl p-hydroxybenzoate, the base and the solvent, in a desired order, and heating and stirring the mixture generally at 60° to 100° C. Preferred examples of the solvent used in step (1) include ketones, such as acetone and 2-butanone, inert ethers, such as THF and diisopropyl ether, and lower alcohols, such as methanol and ethanol. Preferred examples of the base used in step (1) include alkali metal carbonates, such as potassium carbonate and sodium carbonate, and alkali metal hydroxides, such as potassium hydroxide and sodium hydroxide.

Some examples of the compound VII include 4-bromo-1-butene, 4-iodo-1-butene, 4-tosyl-1-butene, 5-bromo-1-pentene, 5-iodo-1-pentene, 5-tosyl-1-pentene, 6-bromo-1-hexene, 6-iodo-1-hexene, 6-tosyl-1-hexene, 7-bromo-1-heptene, 7-iodo-1-heptene, 7-tosyl-1-heptene, 8-bromo-1-octene, 8-iodo-1-octene, 8-tosyl-1-octene, 9-bromo-1nonene, 9-iodo-1-nonene, 9-tosyl-1-nonene, 10-bromo-1-decene, 10-iodo-1-decene, 10-tosyl-1-decene, 11-bromo-1-undecene, 11-iodo-1-undecene, 11-tosyl-1-undecene, 12-bromo-1-dodecene, 12-iodo-1-dodecene, 12-tosyl-1-dodecene, 13-bromo-1-tridecene, 13-iodo-1-tridecene, 13-tosyl-1tridecene, 14-bromo-1-tetradecene, 14-iodo-1-tetradecene, 14-tosyl-1-tetradecene, 15-bromo-1-pentadecene, 15-iodo-1-pentadecene, 15-tosyl-1-pentadecene, 16-bromo-1-hexadecene, 16-iodo-1-hexadecene, 16-tosyl-1-hexadecene, 17-bromo-1-heptadecene, 17-iodo-1-heptadecene, 17-tosyl-1-heptadecene, 18-bromo-1-octadecene, 18-iodo-1-octadecene, 18-tosyl-1-octadecene, 19-bromo-1-nonadecene, 19-iodo-1-nonadecene, 19-tosyl-1-nonadecene, 20-bromo-1-eicosene, 20-iodo-1-eicosene and 20-tosyl-1-eicosene.

Step (2)

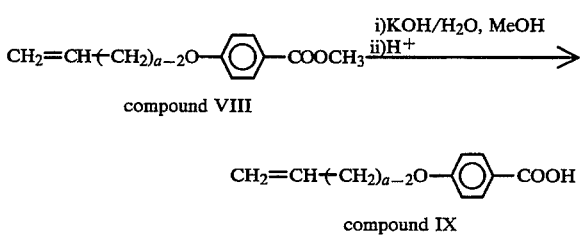

In step (2), only the ester bond in the ester compound (compound VIII) obtained in step (1) is selectively hydrolyzed, to obtain a corresponding carboxylic acid (compound IX). The hydrolysis may be carried out by various methods, and it is suitable to carry out the hydrolysis by treating and, if desired, heating the compound VIII in the presence of a base, in water or in a mixture of water and an alcohol. The compound IX can be collected efficiently by acidifying the obtained reaction solution by adding an acid. Although the hydrolysis may be carried out by heating in the presence of a base catalyst and water, it can be accelerated by further adding an alcohol to improve the solubility of the raw material, i.e. the ester compound. Preferred examples of the base include alkali metal hydroxides, such as potassium hydroxide and sodium hydroxide, and preferred examples of the alcohol include water-soluble lower alcohols, such as methanol and ethanol (EtOH). As to the acid to be used for the adjustment of pH, preferred examples include mineral acids, such as hydrochloric acid and sulfuric acid, which have been commonly used.

Step (3)

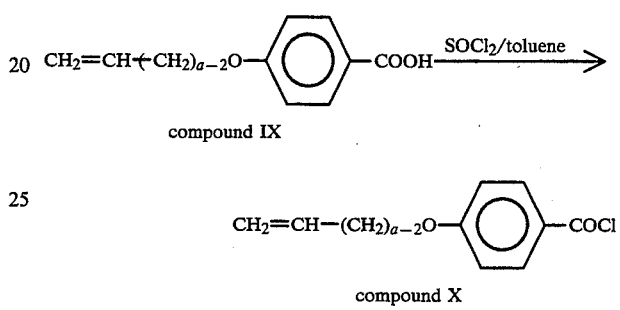

In step (3), the carboxylic acid (compound IX) obtained in step (2) is converted to an acid chloride (compound X) by using a reagent for forming acyl halides, in the absence or presence or a solvent. The reaction for forming the acyl halide may be carried out suitably by known methods. For example, the solvent may be selected from the ones commonly used, such as toluene, and the reagent for forming acyl halides, may be selected from known ones including thionyl chloride, phosphorus oxychloride and phosphorus pentachloride. It is preferable to add a proper amount of a reaction accelerator, such as pyridine.

Step (4)

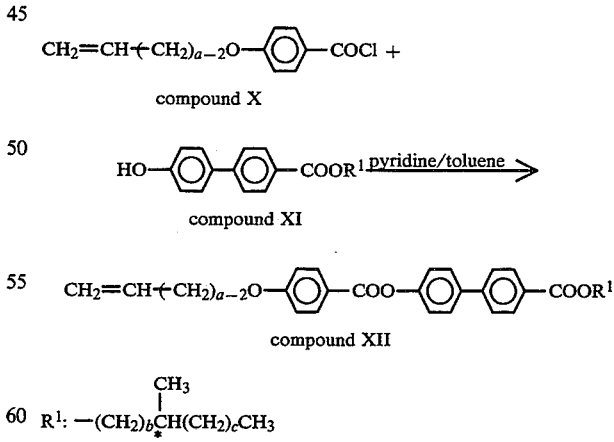

The esterification of the acyl chloride (compound X) and a hydroxy compound (compound XI) is carried out in a solvent in the presence of an acceptor of hydrogen halides, to obtain a compound XII.

The compound XI may be prepared by known methods. The optically active alkyl group at the end of the compound XI can be introduced easily by an esterification using an optically active alcohol (HO—R¹).

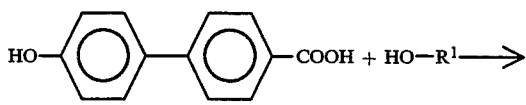

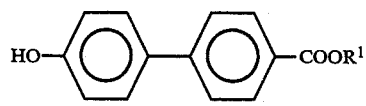

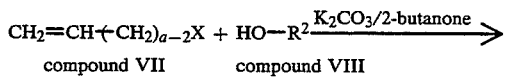

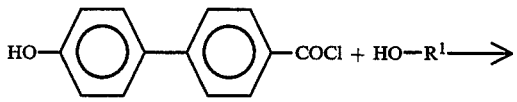

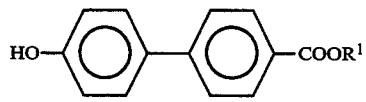

Typical examples of the optically active alcohol (HO—R¹) include (+)-2-methylbutanol, (−)-2-methylbutanol, (+)-2-methylpentanol, (−)-2-methylpentanol, (+)-3-methylpentanol, (−)-3-methylpentanol, (+)-4-methylhexanol, (−)-4-methylhexanol, (+)-2-methylheptanol, (−)-2-methylheptanol, (+)-2-methyloctanol, (−)-2-methyloctanol, (+)-2-butanol, (−)-2-butanol, (+)-2-pentanol, (−)-2-pentanol, (+)-2-hexanol, (−)-2-hexanol, (+)-2-heptanol, (−)-2-heptanol, (+)-2-octanol and (−)-2-octanol.

The esterification in step (4) may be carried out suitably, for example, by introducing a solution comprising the compound XI, an acceptor of hydrogen chlorides and a solvent into the acyl chloride (compound X) obtained in step (3) or a solution thereof, and stirring the mixture. In case the reactivity is low, the reaction mixture may be heated, for example, to 20° to 80° C . Thus, the compound XII can be obtained efficiently.

The acyl chloride (compound X) may be separated to be used in the esterification, or the reaction mixture obtained in step (3) and containing the acyl chloride may be used for the esterification after the removal of the solvent and the reagent for forming acyl halides. Preferred examples of the solvent to be used for the esterification in step (4) include inert ethers, such as THF, and inert hydrocarbons, such as toluene and hexane. Preferred examples of the hydrogen halide acceptors are pyridine and tertiary amines, such as triethylamine (Et₃N).

An example of the alternative to the above-described method of preparing the compound XII is to carry out the etherification of the compound VII and a hydroxy compound (compound XIII) represented by the following Formula (XIII)

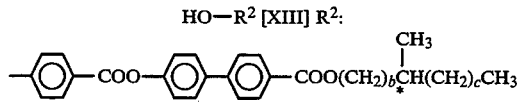

wherein b, c and * are as defined above, in a solvent in the presence of a base. The reaction proceeds, for example, as follows.

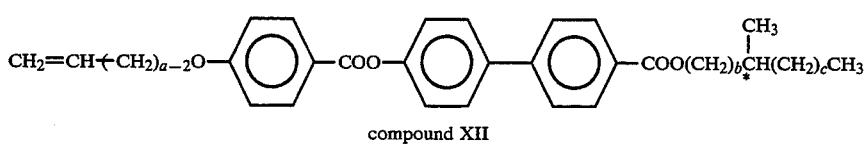

The solvent, base and reaction conditions are the same as those employed in step (1).

Step (5)

(5)-1: In case p=1.

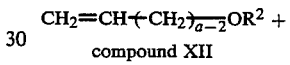

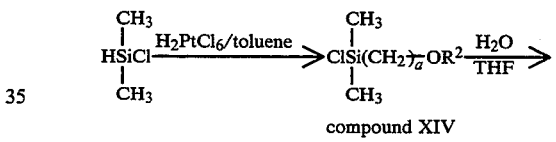

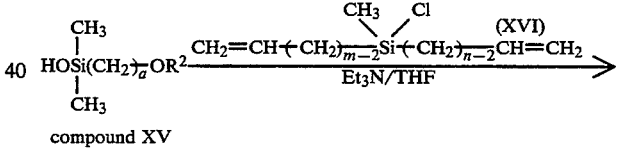

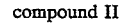

(i) The hydrosilylation of the compound XII with chlorodimethylsilane is carried out in a solvent in the presence of a catalyst to obtain a compound XIV, (ii) the compound XIV is then allowed to react with water to obtain a compound XV, and (iii) the compound XV is allowed to react with a compound XVI in a solvent in the presence of a hydrogen halide acceptor, to obtain the compound II.

The reaction conditions in (i), such as the solvent, the catalyst, the reaction temperature and the way of adding the reagents, are the same as those employed in the above-described copolymerization for the synthesis of the high polymer.

The compound XIV obtained in (i), which tends to decompose, is not separated, and the reaction solution is used for the subsequent reaction (ii) as it is. In (ii), water is dissolved in a solvent compatible with water, such as THF, and is added to the reaction solution containing the compound XIV, in a quantity equimolar to the compound XIV. The reaction temperature may be selected from the range between 0° to 80° C., and in general, the reaction is carried out at room temperature, or during cooling with water. Pyridine or a tertiary amine, such as triethylamine, is added thereto as an acceptor of hydrogen halides. The water may be added to the solvent compatible with water, such as THF, in an excessive amount rather than an equimolar amount, and, after the addition of the reaction solution containing the compound XIV, the residual water may be removed off by using a dehydrating reagent, such as sodium sulfate or magnesium sulfate.

The compound II is obtained by adding a solution of the compound XVI dissolved in an inert ether, such as THF, or an inert hydrocarbon, such as toluene or hexane, to the solution obtained in (ii) and containing the compound XV or to a solution thereof dissolved in an inert ether, such as THF, or an inert hydrocarbon, such as toluene or hexane, followed by the addition of pytidine or a tertiary amine, such as triethylamine, as an acceptor of hydrogen halide and agitating the resulting mixture. The reaction is carried out in an inert gaseous atmosphere, such as $N_2$ or Ar. When the reactivity is low, the reaction system may be heated up to an appropriate temperature ranging from 20° to 8° C.

In place of the chlorodimethylsilane, other alkoxysilanes, such as methoxydimethylsilane and ethoxydimethylsilane, may also be used.

(5)-2: In case P=2

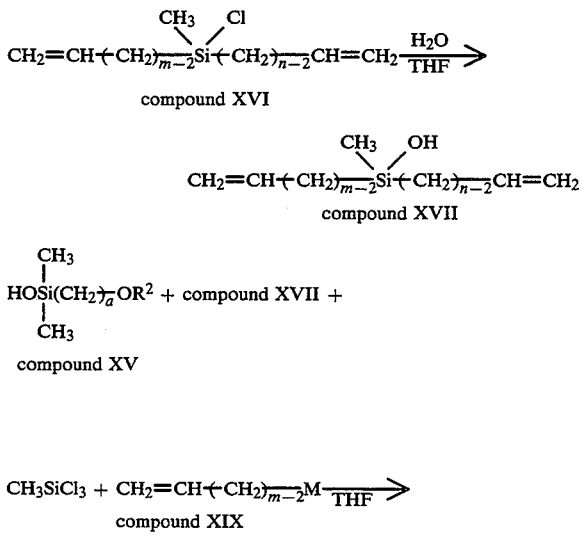

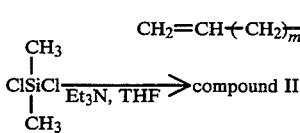

(i) The compound XVI is allowed to react with water, to obtain a compound XVII.

(ii) The compound XVII, the compound XV, which is obtained in (5)-1 of Synthesis-1 of the compound II, and dichlorodimethylsilane are allowed to react in a solvent in the presence of an acceptor of hydrogen halides, to obtain the compound II.

In (i), an equimolar amount of water is dissolved in a solvent compatible with water, such as THF, and the resulting solution is added to the compound XVI. The reaction temperature may be selected from the range from 0° to 80° C., and in general, the reaction is carried out at room temperature, or during cooling with water. Pyridine or a tertiary amine, such as triethylamine, is added thereto as an acceptor of hydrogen halides. The solution obtained in (i) and containing the compound XVII is mixed with the solution obtained in (5)-1 of Synthesis-1 of the compound II and containing the compound XV, and an inert ether, such as THF, or an inert hydrocarbon, such as toluene or hexane, is added thereto according to demand. To the mixture is added a solution of dichlorodimethylsilane dissolved in an inert ether solvent, such as THF, or an inert hydrocarbon solvent, such as toluene or hexane, and then pyridine or a tertiary amine, such as triethylamine, is added thereto as an acceptor of hydrogen halides. The resulting mixture is stirred to obtain the compound II. The reaction is carried out in an inert gaseous atmosphere, such as nitrogen or argon, at room temperature, or during cooling with water. When the reactivity is low, the reaction system may be heated up to an appropriate temperature ranging from 20° to 80° C.

Step (6)

The compound XVI may be synthesized by the following method (i) or (ii).

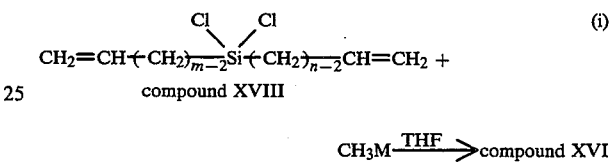

An equimolar reaction of a dialkenyldichlorosilane (XVIII) with an organic metal compound, such as methyllithium (M=Li) or methylmagnesium bromide (M=MgBr), is carried out in an inert ether, such as THF, or an inert hydrocarbon, such as toluene or hexane, to obtain a compound XVI. The reaction is carried out in an atmosphere of an inert gas, such as $N_2$ or Ar. Although the reaction may be carried out at a temperature ranging from −70° C. to 80° C., it is generally carried out at a temperature of 0° to 30° C . As to the method of adding each reagent, it is preferable to add dropwise a solution of methyllithium dissolved in the above-described solvent to a solution of the compound XVIII dissolved in the above-described solvent.

(ii)

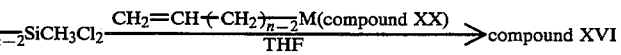

A compound XVI is obtained by an approximately equimolar reaction of trichloromethylsilane with a compound XIX, followed by an approximately equimolar reaction with a compound XX. The reaction conditions, such as the solvent and reaction temperature, are the same as those employed in (i) of step (6) . Some examples of the compound XIX and compound XX include vinyllithium, allyllithium, vinylmagnesium bromide., allylmagnesium bromide, 3-butenylmagnesium bromide and 4-pentenylmagnesium bromide. For the synthesis of the compound II, the compound XVI does not necessarily require purification and may be used in a state of a solution after the filtering off of the solid matters formed by the reaction.

As to the compound XVIII used in (i), alkoxysilanes, such as methoxysilane and ethoxysilane, may also be used in place of the chlorosilane. The trichloromethylsilane used in (ii) also may be replaced by alkoxysilanes, such as trimethoxymethylsilane and triethoxymethylsilane.

Synthesis-2 of the compound II

The following method is an alternative method for the synthesis of the compound II.

Step (1)

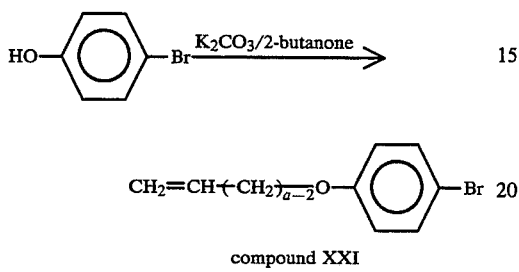

compound XXI

A compound XXI is obtained by allowing a mixture of the compound VII and p-bromophenol to react, in a solvent, in the presence of a base. The reaction conditions and reagents to be used are the same as those employed in step (1) of synthesis-1 of the compound II with the exception that the methyl p-hydroxybenzoate used in step (1) of Synthesis-1 of the compound II is replaced by p-bromophenol. p-Iodophenol or p-chlorophenol may be used in place of the p-bromophenol to obtain an iodized or chlorinated compound, which is to be used in the following step (2) in place of the brominated compound XXI.

Step (2)

Step (2)-1: In case p=1

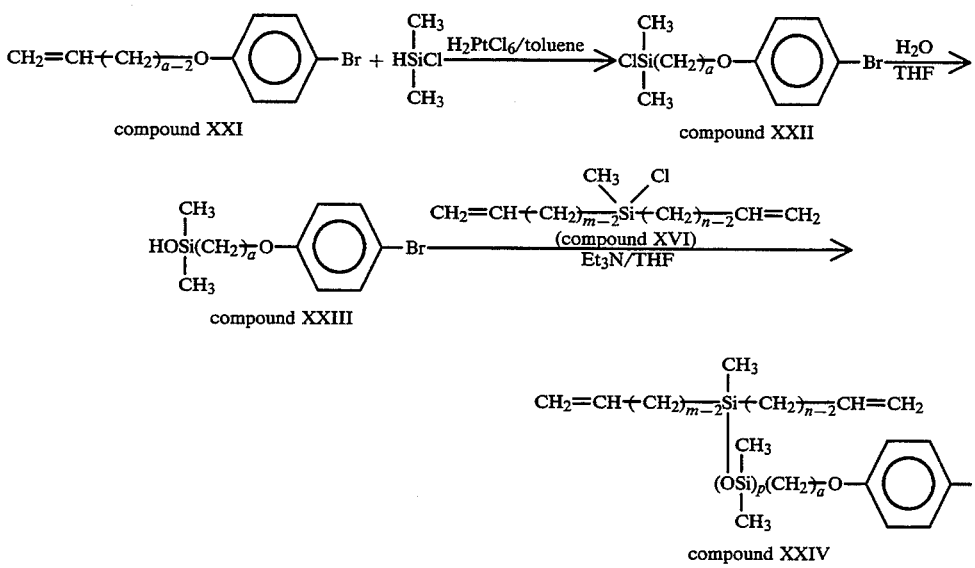

(i) A hydrosilylation of the compound XXI with chlorodimethylsilane is carried out in a solvent in the presence of a catalyst to obtain a compound XXII, (ii) the compound XXII is allowed to react with water to obtain a compound XXIII, and (iii) the compound XXIII is allowed to react with a compound XVI in a solvent in the presence of an appropriate acceptor of hydrogen halides, to obtain a compound XXIV.

The reaction conditions and reagents to be used in this step are the same as those used in step (5)-1 of Synthesis -1 of the compound II with the exception that the compound XII is replaced by the compound XXI, the compound XIV by the compound XXII, the compound XV by the compound XXIII, and the compound II by the compound XXIV. The brominated compound XXI may be replaced by a corresponding iodized or chlorinated compound, to obtain an iodized or chlorinated compound, which is to be used in the following step (3) in place of the brominated compound XXIV.

Step (2)-2: In case p=2

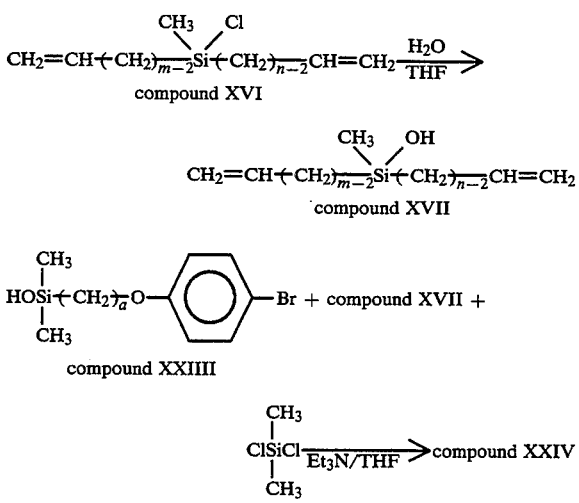

(i) A compound XVI is allowed to react with water to obtain a compound XVII.

(ii) The compound XVII, the compound XXIII obtained in Step (2)-1 of Synthesis-2 of the compound II and dichlorodimethylsilane are allowed to react in a solvent in the presence of an appropriate acceptor of hydrogen halides, to obtain a compound XXIV.

In (i), water dissolved in a solvent compatible with water, such as THF, is added to the compound XVI in equimolar amounts. The reaction temperature may be selected from temperatures ranging from 0° to 80° C., and the reaction is carried out generally at room temperature or during cooling with water. A tertiary amine, such as pyridine or triethylamine, is added as an acceptor of hydrogen halides.

The compound XXIV is obtained by mixing the solution obtained in (i) and containing the compound XVII and the solution which is obtained in Step (2)-1 of Synthesis-2 of the compound II and contains the compound XXIII, adding to the mixture an inert ether, such as THF, or an inert hydrocarbon, such as toluene or a hexane, according to demand, adding thereto a solution of dichlorodimethylsilane dissolved in an inert ether, such as THF, or an inert hydrocarbon, such as toluene or hexane, further adding thereto pyridine or a tertiary amine, such as triethylamine, as an acceptor of hydrogen halides, and stirring the resulting mixture. The reaction is carried out in an atmosphere of an inert gas, such as nitrogen or argon, at room temperature or during cooling with water When the reactivity is low, the reaction system may be heated up to an appropriate temperature ranging from 20° to 80° C.

The brominated compound XXI may be replaced by a corresponding iodized or chlorinated compound, to obtain an iodized or chlorinated compound, which is to be used in the following step (3) in place of the brominated compound XXIV.

Step (3)

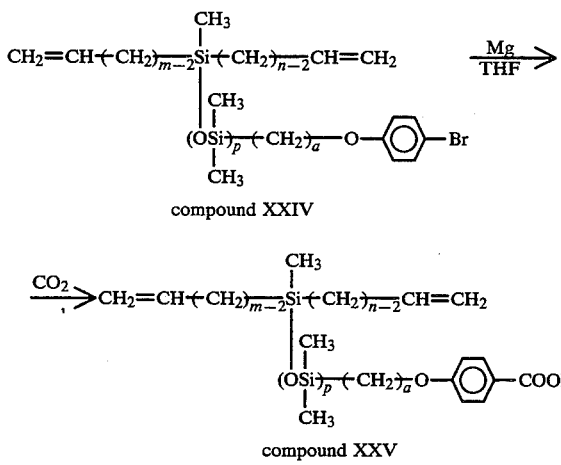

(i) The compound XXIV is allowed to react with magnesium in a solvent to obtain a Grignard reagent, which is then allowed to react with carbon dioxide to obtain a compound XXV.

Preferred examples of the solvent used in (i) include inert ethers, such as THF. The reaction may be accelerated by adding, For example, $I_2$ or 1,2-dibromoethane. The reaction is carried out in an atmosphere of an inert gas, such as nitrogen or argon, at room temperature or a temperature elevated up to 20° to 80° C. The reaction in (ii) may be carried out by bubbling carbon dioxide in the reaction solution of (i), or by adding the reaction solution of (i) to dry ice .

Step (4)

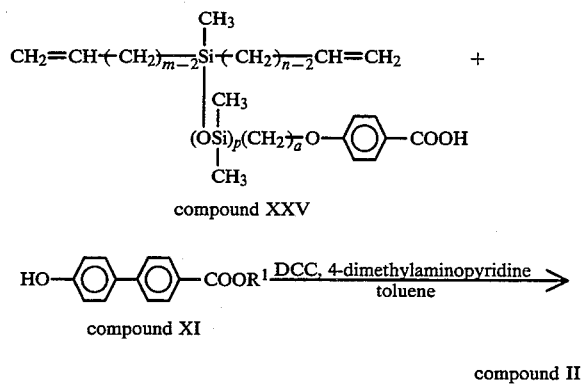

The compound XXV is allowed to react with a compound XI by using a condensing agent, such as DCC, to obtain the compound II. The reaction may be accelerated by adding, for example, 4-dimethylaminopyridine. Some examples of the solvent to be used include toluene and methylene chloride. The reaction is carried out in an atmosphere of an inert gas, such as nitrogen or argon. The reaction may be carried out at 0° to 80° C., generally at room temperature.

The above-described silicon compound (compound VI) to be used as a material for the preparation of the high polymer of the present invention has two Si—H bonds, and those, where in

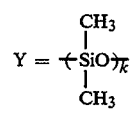

and k is 1, 2 or 3, are substantially free of the distribution in the value of k. On the other hand, those wherein k has a large value have distributed polymerization degrees (distributed values of k), and the value of k, therefore, is represented by an average value. Therefore, the values of k of the high polymers prepared from the latter ones are also average values. Some typical examples of the compound VI include 1,1,3,3-tetramethyldisiloxane, 1,1,3,3,5,5-hexamethyltrisiloxane, 1,1,3,3,5,5,7,7-octamethyltetrasiloxane, α,ω-hydrogen-oligodimethyl-siloxanes of 6 or 7 silicon atoms, 1,1-bis(dimethylsilyl)methane, 1,1,4,4-tetramethyldisilethylene, 1,3-bis(-dimethylsilyl)propane and 1,4-bis(dimethylsilyl)butane. In the above-described copolymerization, these compounds VI may be used individually or, according to demand, as a mixture of two or more of them.

The novel high polymer of the present invention may be prepared suitably by the above-described method of preparing the high polymer using compound II and compound VI which are synthesized as described above.

The present invention also provides a ferroelectric liquid-crystalline composition comprising the novel high polymer of the present invention and a low molecular weight smectic liquid-crystalline compound.

The ferroelectric liquid-crystalline composition of the present invention is obtained by mixing the novel high polymer and a low molecular weight smectic liquid-crystalline compound.

There is no particular limitation in the kind of the low molecular weight smectic liquid-crystalline compound, and one or more ones selected from known ones may be used. Some examples of the low molecular weight liquid-crystalline compound include

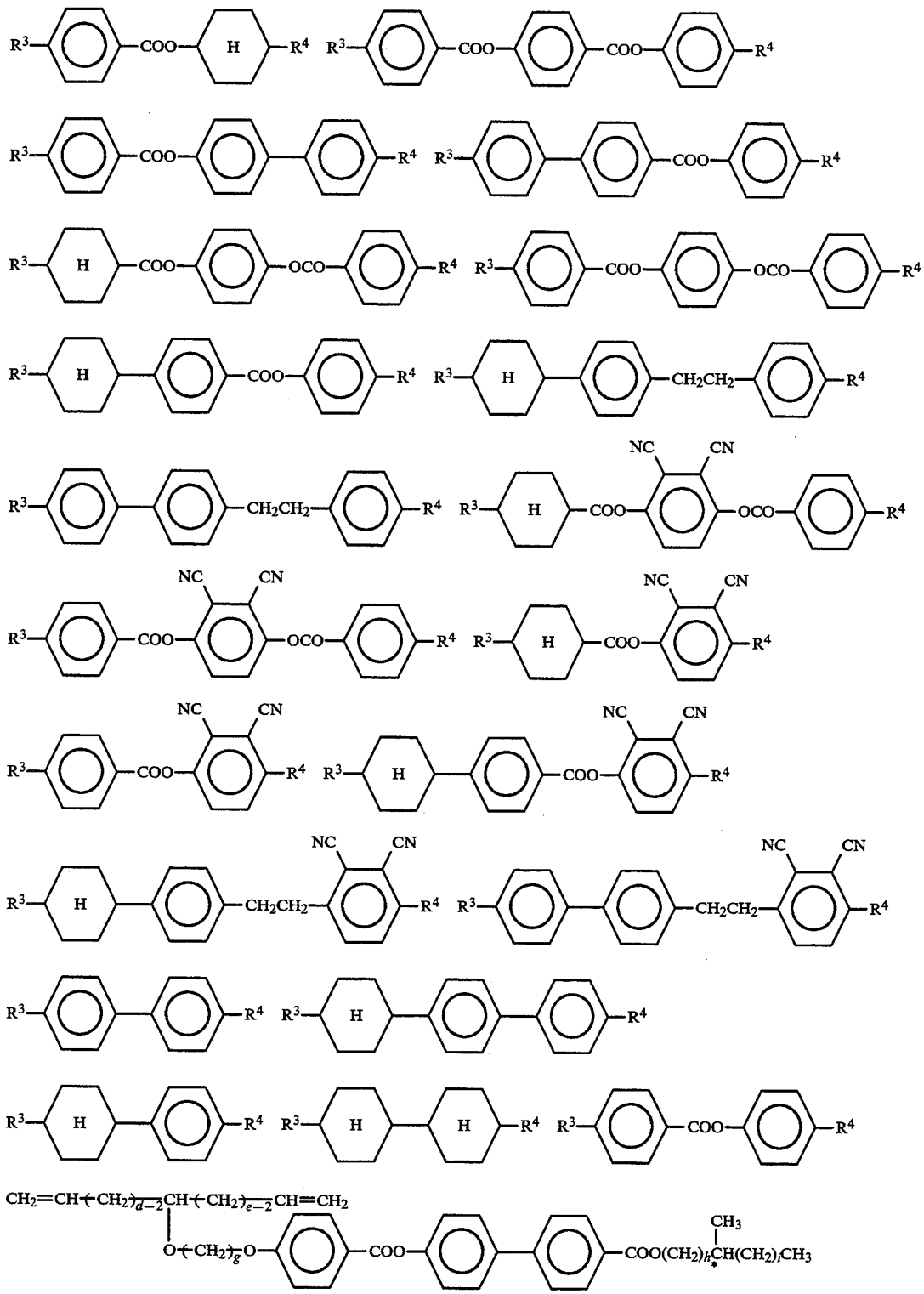

wherein each of $R^3$ and $R^4$ respectively is a linear or branched alkyl, alkoxy, alkoxycarbonyl or acyloxy group of 1 to 12 carbon atoms, and these may be identical with or different from each other, each of d and e is an integer of 2 to 5, g is an integer of 8 to 12, h is an integer of 0 to 3, i is an integer of 1 to 7, and * indicates an asymmetric carbon atom, and the diene compound represented by the formula (II) which is used for the synthesis of the novel high polymer of the present invention.

Further, the compounds represented by the following formulas

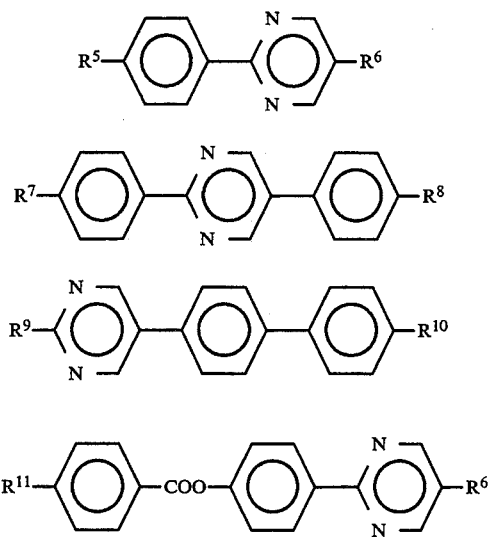

also may be used. In the Formula (XXVI), $R^5$ is an alkyl group of 7 to 12 carbon atoms, an alkoxy group of 6 to 15 carbon atoms or an alkoxycarbonyl or acyloxy group of 6 to 12 carbon atoms. In the formulas (XXVI) and (XXIX), $R^6$ is an alkyl group of 7 to 12 carbon atoms or an alkoxy group of 6 to 11 carbon atoms. In the formula (XXVII), each of $R^7$ and $R^8$ respectively is an alkyl or an alkoxy group of 4 to 14 carbon atoms, and they may be identical with or different from each other. In the formula (XXVIII), $R_9$ is an alkyl group of 4 to 14 carbon atoms, and $R^{10}$ is an alkyl group of 5 to 14 carbon atoms or an alkoxy group of 4 to 14 carbon atoms. In the formula (XXIX), $R^{11}$ is an alkyl group of 7 to 12 carbon atoms or an alkoxy group of 6 to 20 carbon atoms. The methylene groups in $R^5$ and $R^{11}$ may be partially substituted by ester groups or oxygen atoms with the proviso that there is no continuation of ester groups or oxygen atoms. Also, each of $R^5$ to $R^{11}$ may be linear or branched.

Some typical examples of these low molecular weight smectic liquid-crystalline compounds include the Followings.

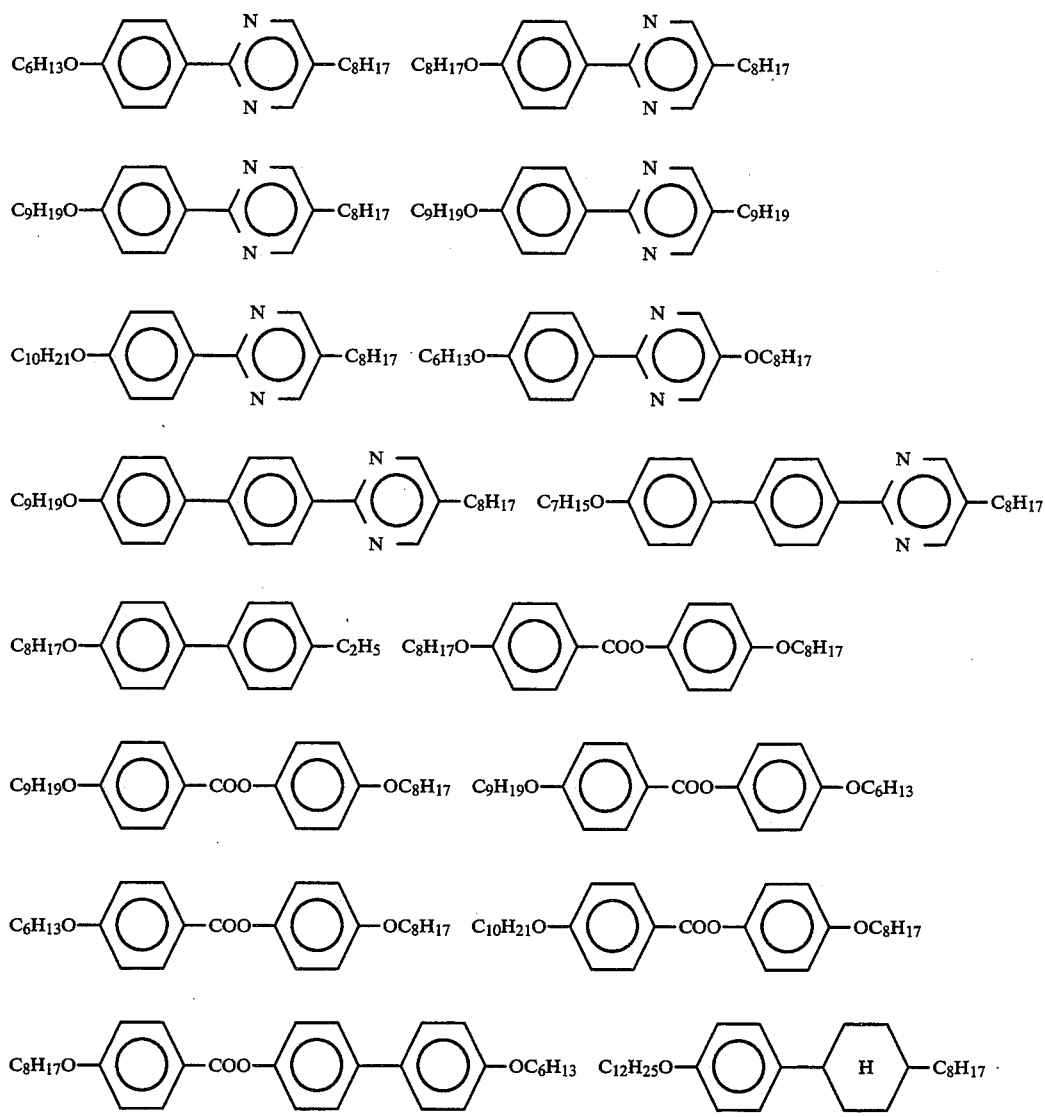

-continued

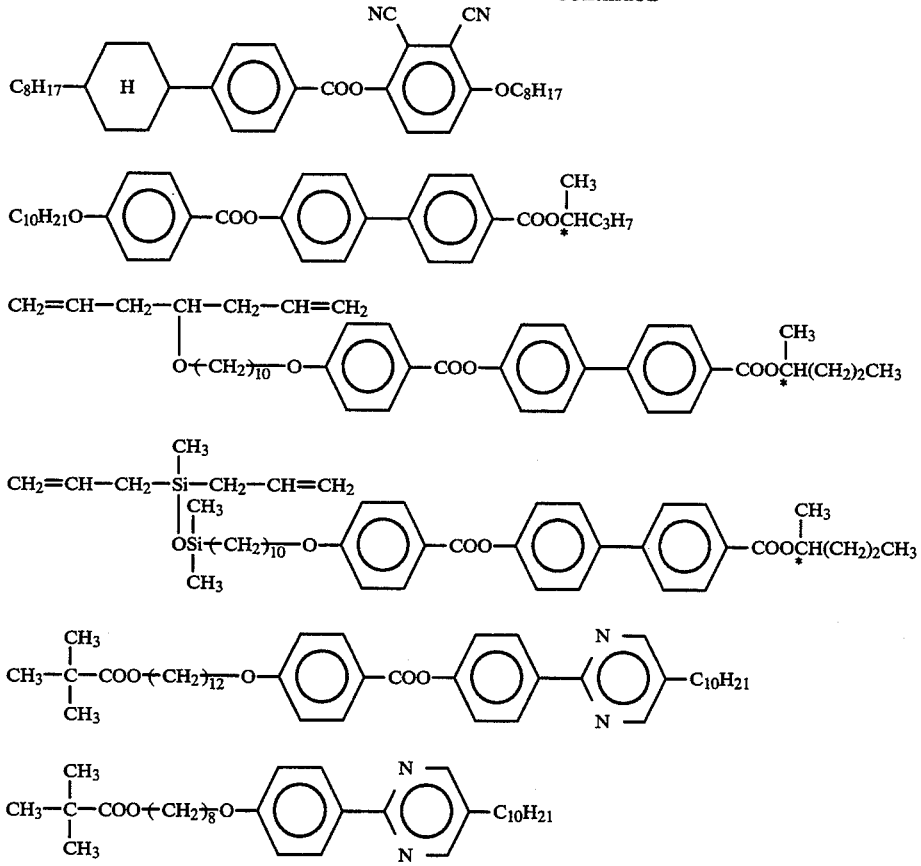

Since the novel high polymer has a comb-structure, in the ferroelectric liquid-crystalline composition of the present invention, the low molecular weight smectic liquid-crystalline compound occludes the space between the side chains of the high polymer, so as to form a uniform mixture wherein they are dissolved in each other. FIG. 1 is a schematic view illustrating such a situation, wherein a referential number 1 represents the novel high polymer of the present invention, and a referential number 2 represents the low molecular weight smectic liquid-crystalline compound.

Since the ferroelectric liquid-crystalline composition of the present invention forms a uniform mixture as described above, it exhibits a high contrast ratio and responds to external factors at a great speed. Further, due to the presence of the high polymer, it can be oriented easily and uniformly to a desired oriented state, thereby facilitating the production of liquid crystal optical devices.

Further, even if the liquid-crystalline composition of the present invention contained a non-chiral smectic liquid crystals as the low molecular weight smectic liquid-crystalline compound, the composition can form a ferroelectric phase since the optically active group introduced in the high polymer having a comb-structure causes the high polymer to function as a chiral dopant.

The high polymer of the present invention itself does not necessarily form $S_C^{**}$ phase since the functions essential to the high polymer in the ferroelectric liquid-crystalline composition of the present invention are to function as a chiral dopant and to provide the composition with moldability and the capability to be oriented easily and uniformly.

A high polymer comprising the following repeating unit (III) also may be added as an additional composition to the ferroelectric liquid-crystalline composition of the present invention.

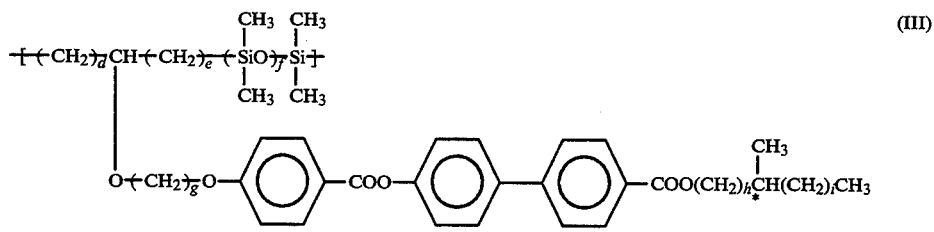

(III)

wherein, each of d and e is an integer of 2 to 5, f is a number of 1 to 6, g is an integer of 8 to 12, h is an integer of 0 to 3, i is an integer of 1 to 7, and * represents an asymmetric carbon atom.

The high polymer (III) forms $S_C^{**}$ phase over a wide range of temperatures including room temperature and, in common with the novel high polymer of the present invention, has a flexible siloxane chain in its main chain and provides a wide space between its side chains.

Therefore, adding the high polymer (III) to the high polymer of the present invention and the low molecular weight smectic liquid-crystalline compound provides a ferroelectric liquid-crystalline compound having good moldability and the capability to be oriented easily and uniformly, with the uniformly mixed state of the composition maintained.

The high polymer (III) may be prepared, for example, by carrying out a hydrosilylation of a diene compound (XXX) and a silicon compound (XXXI), which are represented by the following Formulas:

amount of the novel high polymer exceeds 99% by weight, the response time against the change of electric field may be prolonged.

In case the high polymer (III) is added, the preferred total amount of the high polymer (I) and (III) is 5 to 99% by weight, preferably 20 to 80% by weight. The preferred amount of the novel high polymer of the present invention in the total of the high polymers is 40 to 99 by weight. If the amount of the novel high polymer of the present invention is less than 40% by weight, the response time against the change of electric field

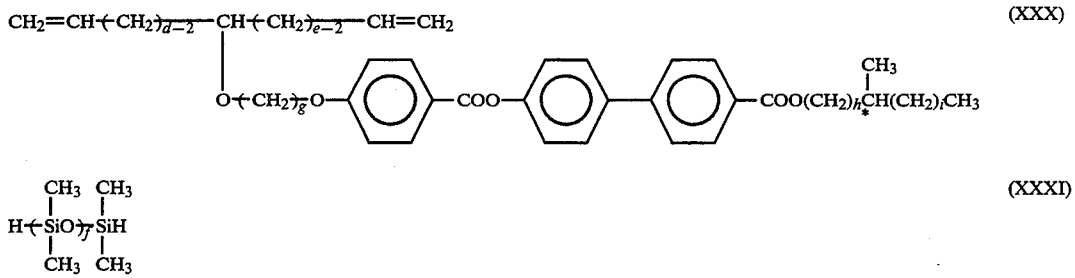

wherein d, e, f, g, h, i and * are as defined above, in a solvent in the presence of a catalyst.

Preferred examples of the solvent to be used in the hydrosilylation of the compound (XXX) and the compound (XXXI) include inert aromatic hydrocarbons, such as benzene, toluene and xylene, and inert ethers, such as THF and diisopropyl ether. Preferred examples of the catalyst to be used in the reaction include platinum catalysts, such as hydrogen hexachloroplatinate (IV), platinum(II) acetylacetonate and dicyclopentadienylplatinum chloride. It is preferable to carry out the reaction in an inert atmosphere at 60° to 90° C. for 5 to 20 hours.

The method of mixing the high polymers with the low molecular weight smectic liquid-crystalline compound is not particularly limited, and a direct mixing or a solution mixing may be employed. For example, it is suitable to employ a solution mixing, wherein predetermined amounts of the high polymers and the low molecular weight smectic liquid-crystalline compound are introduced in a vessel, in which they are dissolved in a solvent, such as dichloromethane, and the solvent is then evaporated.

In case the high polymer (III) is not added, the preferred amount of the novel high polymer mixed in the composition is 5 to 99% by weight, preferably 20 to 80% by weight. If the amount of the novel high polymer is less than 5% by weight, the liquid-crystalline compound may be insufficient in the moldability into film and in the capability to be oriented easily and uniformly. Further, in case the low molecular weight smectic liquid-crystalline compound is non-chiral, the composition may not form a ferroelectric phase. If the may be prolonged.

The ferroelectric liquid-crystalline composition of the present invention may further contain additives, such as pigments and adhesives.

Examples of the present invention are set forth below. It will be understood that these examples are for purposes of illustration only and are not to be construed as limiting the invention.

EXAMPLES 1 TO 17

In Examples 1 to 11, the electric field response time ($\tau$) means the time required by the intensity of transmitted light to be changed from 10 to 90% by the application of a rectangular voltage of $\pm 10$ V/$\mu$m at 25° C. Other conditions were the same as those employed in Example 11.

The symbols in the formulas showing phase transition behavior, have the following meanings. glass: glass phase, $S_C^{}$: chiral smectic C phase, Iso: isotropic phase, $S_A$: smectic A phase, $N^{}$: chiral nematic phase, Cryst: crystal phase.

Phase transition temperature was determined by microscopic observation in the manner as described in Example 11. The numerals in the formulas showing phase transition behavior means temperatures in °C. In the Following Examples, Mw means weight average molecular weight (polystyrene conversion) measured by GPC (gel permeation chromatography).

EXAMPLE 1

Synthesis of high polymer (A)

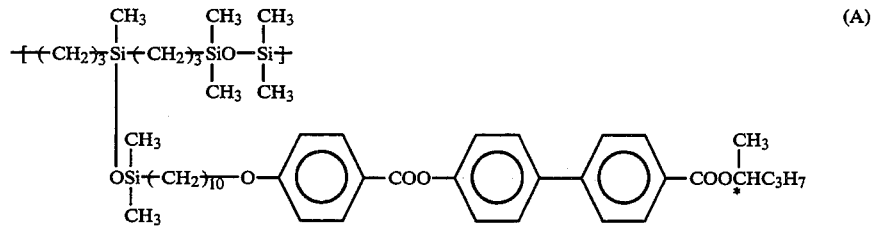

[1] Synthesis of compound (1)

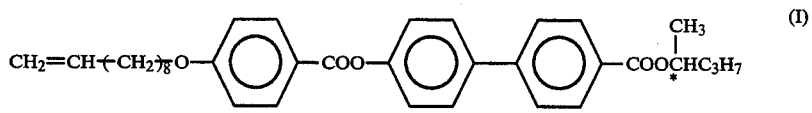

(I)

4 ml of thionyl chloride was added to 8.0 g of 4-(9-decenyloxy)benzoic acid, and the mixture was stirred for 4 hours at 65° C. After the excessive thionyl chloride was distilled off under reduced pressure, 20 ml of toluene was added. Thereto was dropped a solution of 9.1 g of (S)-1-methylbutyl 4-hydroxybiphenyl-4'-carboxylate and 2.8 g of pyridine dissolved in 20 ml of toluene, and were allowed to react at room temperature for a day. The insoluble matters formed therein were filtered off, and the solvent was distilled off under reduced pressure. Recrystallization from ethanol was carried out to obtain 11.7 g of the objective compound (1) (Yield: 74%).

[2] Synthesis of monomer (a)

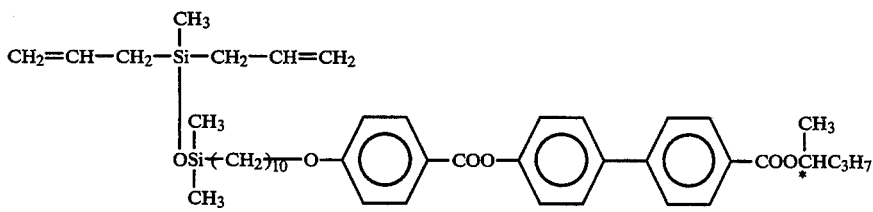

(a)

1.0 g of diallyldichlorosilane was dissolved in 10 ml of THF, and 3.6 ml of a 1.4M solution of methyl lithium dissolved in diethyl ether was added thereto dropwise in an atmosphere of argon during cooling with water. The mixture was stirred for three hours during cooling with water. The solid matters formed therein were removed off to obtain an ether solution of diallylchloromethylsilane (2).

At the same time, 1.0 g of the compound (1) was dissolved in 2 ml of toluene, and thereto were added 0.35 g of chlorodimethylsilane and 20 μl of 4% by weight 2-propanol solution of hydrogen hexachloroplatinate (IV) hexahydrate. The mixture was stirred in an atmosphere of argon at 100° C. for four hours to obtain a chlorosilane compound (3). To the reaction solution were added a solution of 36 mg of water and 0.20 g of triethylamine dissolved in 10 ml of THF, and the mixture was stirred for 10 minutes during cooling with water, to obtain a silanol compound (4).

Figure 2:
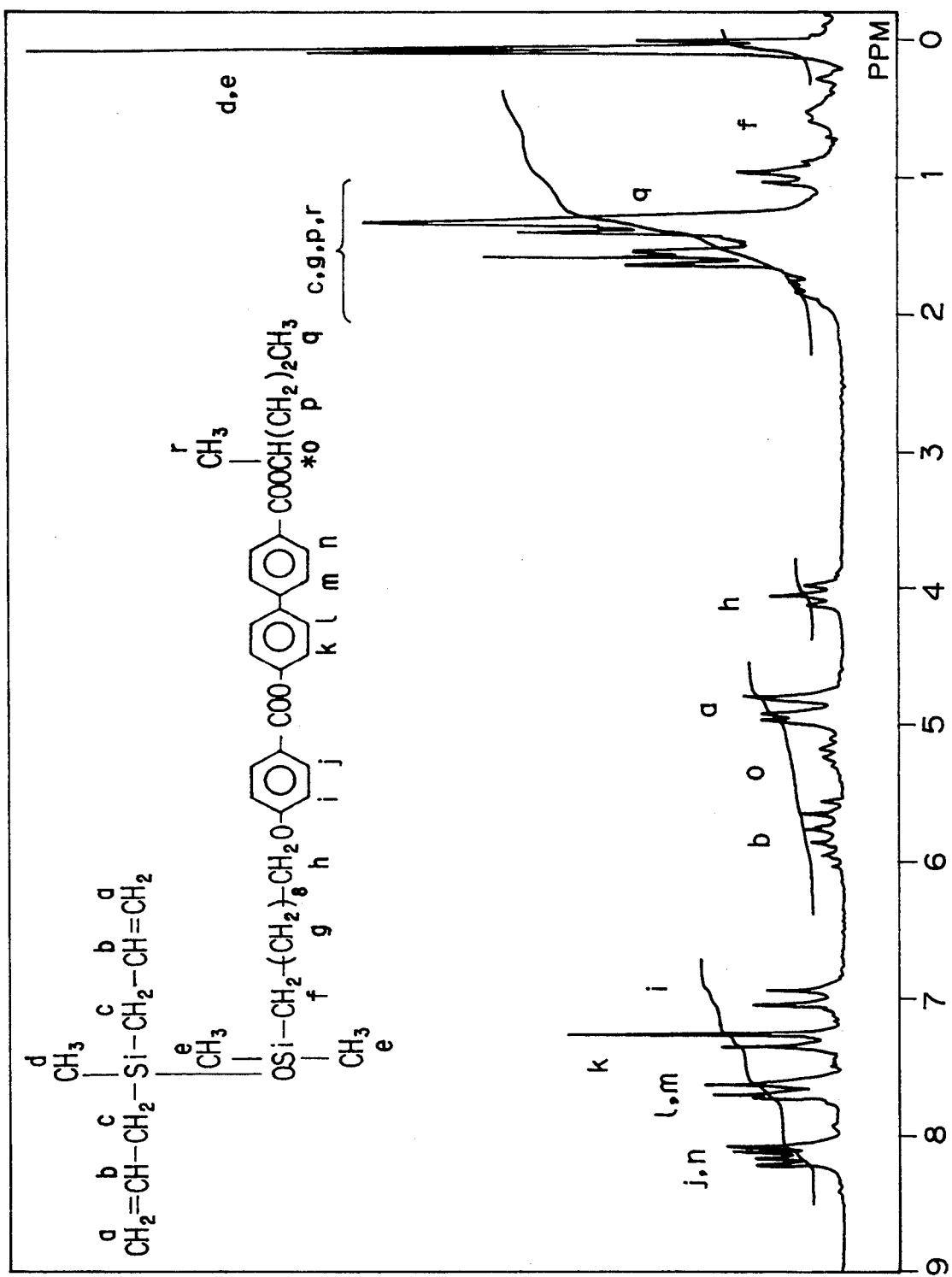
FIG. 2 is a $^1$H-NMR chart of monomer (a) obtained in Example 1.

To the reaction solution were added dropwise the above-described ether solution of the diallylchloromethylsilane (2) and a solution of 0.56 g of triethylamine dissolved in 5 ml of THF, in an atmosphere of argon during cooling with water. Thereafter, reaction was carried at room temperature for two days. After washing with a saline solution and drying over magnesium sulfate, the solvent was distilled off under reduced pressure. The residue was purified by a silica gel column chromatography to obtain 0.60 g of the objective monomer (a) (Yield: 44%). The $^1$H-NMR chart and properties of monomer (a) are shown in FIG. 2 and Table 1, respectively.

Figure 3:
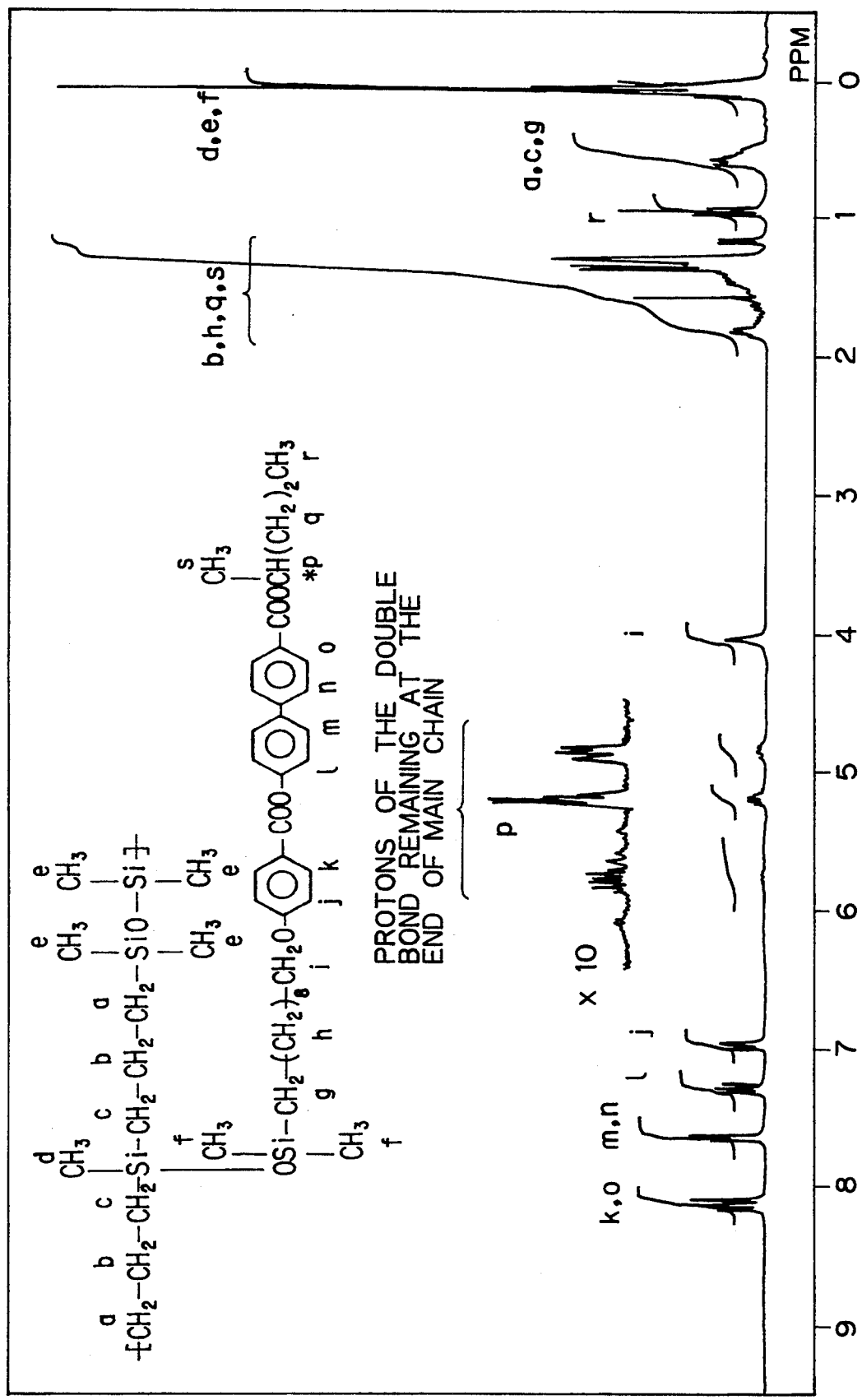
FIG. 3 is a $^1$H-NMR chart of high polymer A obtained in Example 1.

[3] Polymerization 0.40 g of monomer (a) was dissolved in 5 ml of toluene, and the atmosphere was replaced by argon. After the addition of 98 mg of 1,1,3,3-tetramethyldisiloxane and 30 μl of a 4% by weight 2-propanol solution of hydrogen hexachloroplatinate (IV) hexahydrate, reaction was carried out at 85° C. for 17 hours. After the solvent was distilled off under reduced pressure, the residue was purified by a silica gel column chromatography, to obtain 0.43 g of high polymer A (Yield: 86%). The $^1$H-NMR chart and properties of high polymer A are shown in FIG. 3 and Table 2, respectively.

EXAMPLE 2

Synthesis of high polymer B

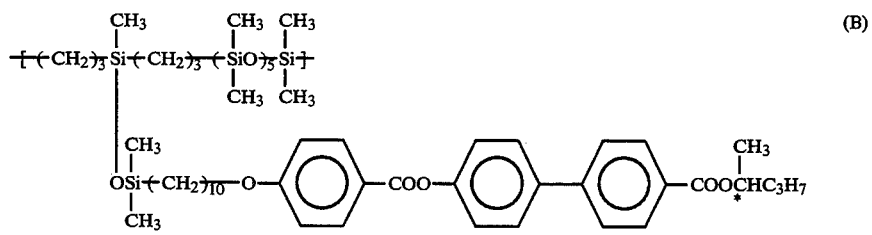

(B)

Figure 4:
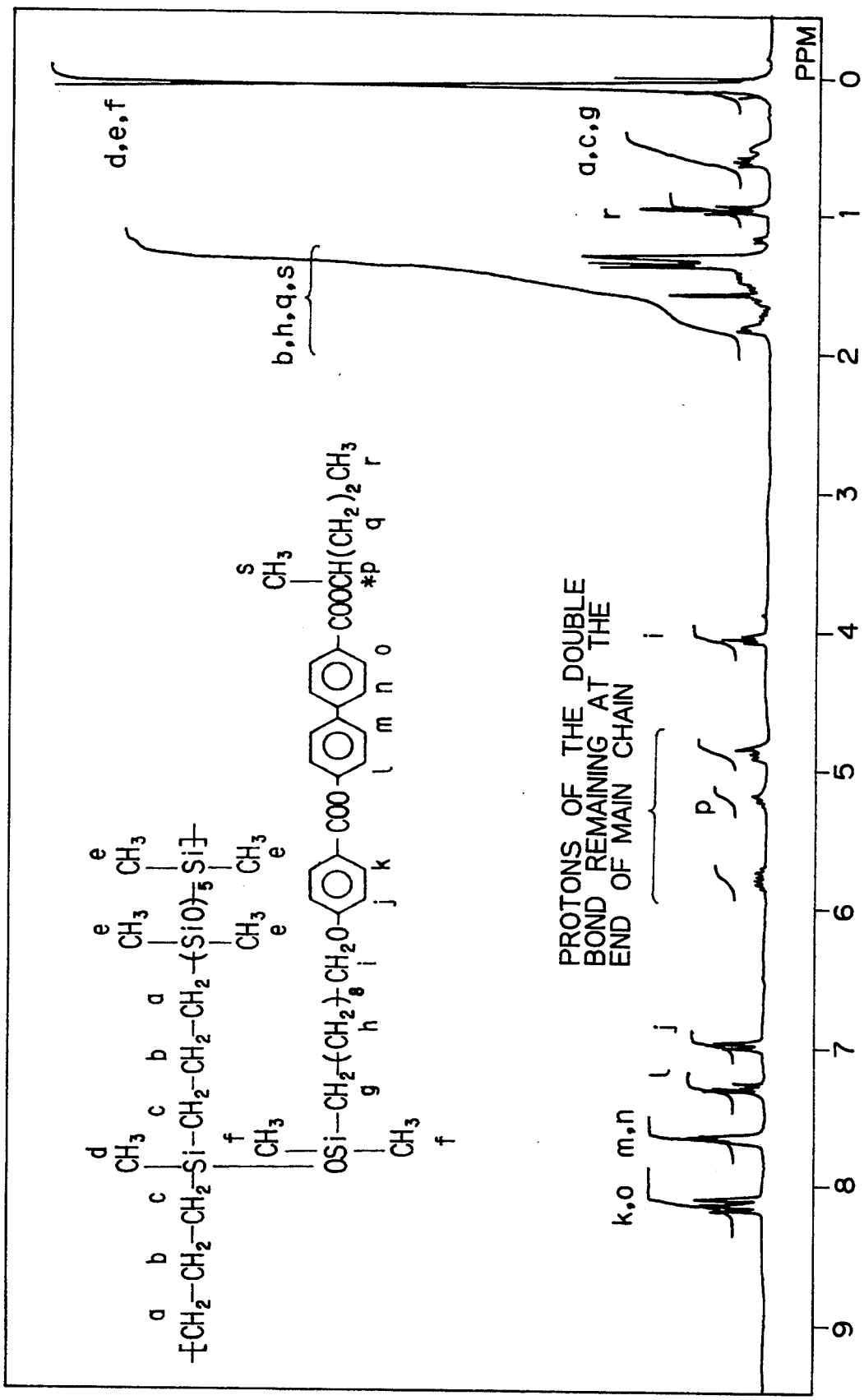
FIG. 4 is a $^1$H-NMR chart of high polymer B obtained in Example 2.

0.39 g of monomer (a) obtained in the same manner as in Example 1 was dissolved in 5 ml of toluene, and the atmosphere was replaced by argon. After the addition of 0.16 g of an α,ω-hydrogen-oligodimethylsiloxane (weight average molecular weight: 670) and 20 μl of a 4% by weight 2-propanol solution of hydrogen hexachloroplatinate (IV) hexahydrate, reaction was carried out at 85° C. for 10 hours. After the solvent was distilled off under reduced pressure, the residue was purified by a silica gel column chromatography, to obtain 0.45 g of high polymer B (Yield: 82%). The $^1$H-NMR chart and properties of high polymer B are shown in FIG. 4 and Table 2, respectively.

EXAMPLE 3

Synthesis of high polymer C

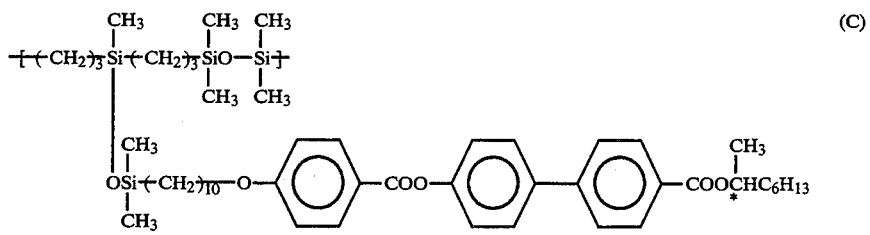

(C)

[1] Synthesis of compound (5)

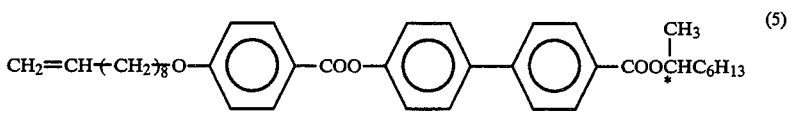

(5)

7 ml of thionyl chloride was added to 4.0 g of 4-(9-decenyloxy)benzoic acid, and the mixture was stirred at 65° C. for 6 hours. After the excessive thionyl chloride was distilled off under reduced pressure, 10 ml of toluene was added. Thereto were added dropwise a toluene solution of 5.2 g of (S)-1-methylheptyl 4-hydroxybiphenyl-4'-carboxylate and 1.4 g of pyridine dissolved in 15 ml of toluene, at room temperature, and reaction was carried out for a day at room temperature. The insoluble matters formed therein were filtered off, and the solvent was distilled off under reduced pressure. The residue was recrystallized from ethanol, to obtain 6.2 of the objective compound (5) (Yield: 73%)

[2] Synthesis of monomer (b)

4.7 of diallydichlorosilane was dissolved in 35 ml of THF, and thereto was added dropwise 20 ml of a 1.4M diethyl ether solution of methyl lithium in an atmosphere of argon over a 10 minutes interval. The mixture was then stirred for three hours during cooling with water. The solid matters formed therein were removed off to obtain an ether solution of diallylchloromethylsilane (2).

At the same time, 5.0 g of compound (5) was dissolved in 10 ml of toluene, and thereto were added 2.4 g of chlorodimethylsilane and 70 μl of a 4% by weight 2-propanol solution of hydrogen hexachloroplatinate (IV) hexahydrate. The mixture was then stirred in an atmosphere of argon at 100° C. for four hours, to obtain chlorosilane compound (6). The reaction solution was added to a solution mixture of 240 ml of THF and 16 ml of water, and the mixture was allowed to stand at room temperature for 10 minutes, to obtain silanol compound (7).

Figure 5:
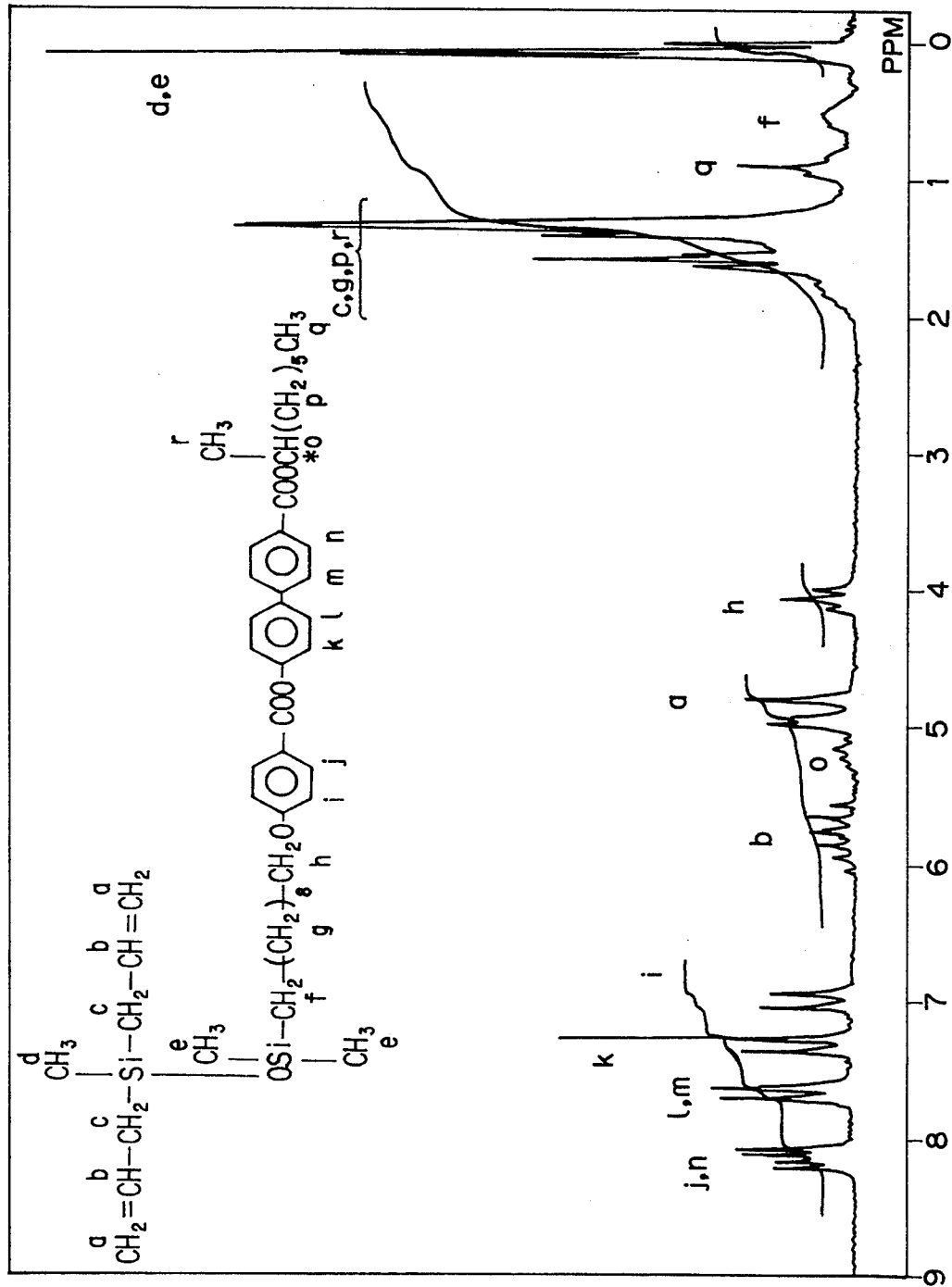
FIG. 5 is a $^1$H-NMR chart of monomer (b) obtained in Example 3.

After the reaction solution was dried over magnesium sulfate, the above-described ether solution of diallylchloromethylsilane (2) and 2.1 g of triethylamine were added dropwise in an atmosphere of argon during cooling with water. Reaction was then carried out For two days during cooling with water. After the solid matters formed therein were filtered off, the reaction solution was washed with a saline solution and dried over magnesium sulfate, and the solvent was then distilled off under reduced pressure. The residue was purified by a silica gel column chromatography to obtain 0.78 g of the objective monomer (b) (Yield: 12%). The $^1$H-NMR chart and properties of monomer (b) are shown in FIG. 5 and Table 1, respectively.

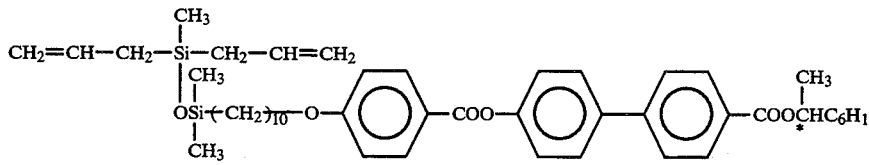

(b)

Figure 6:
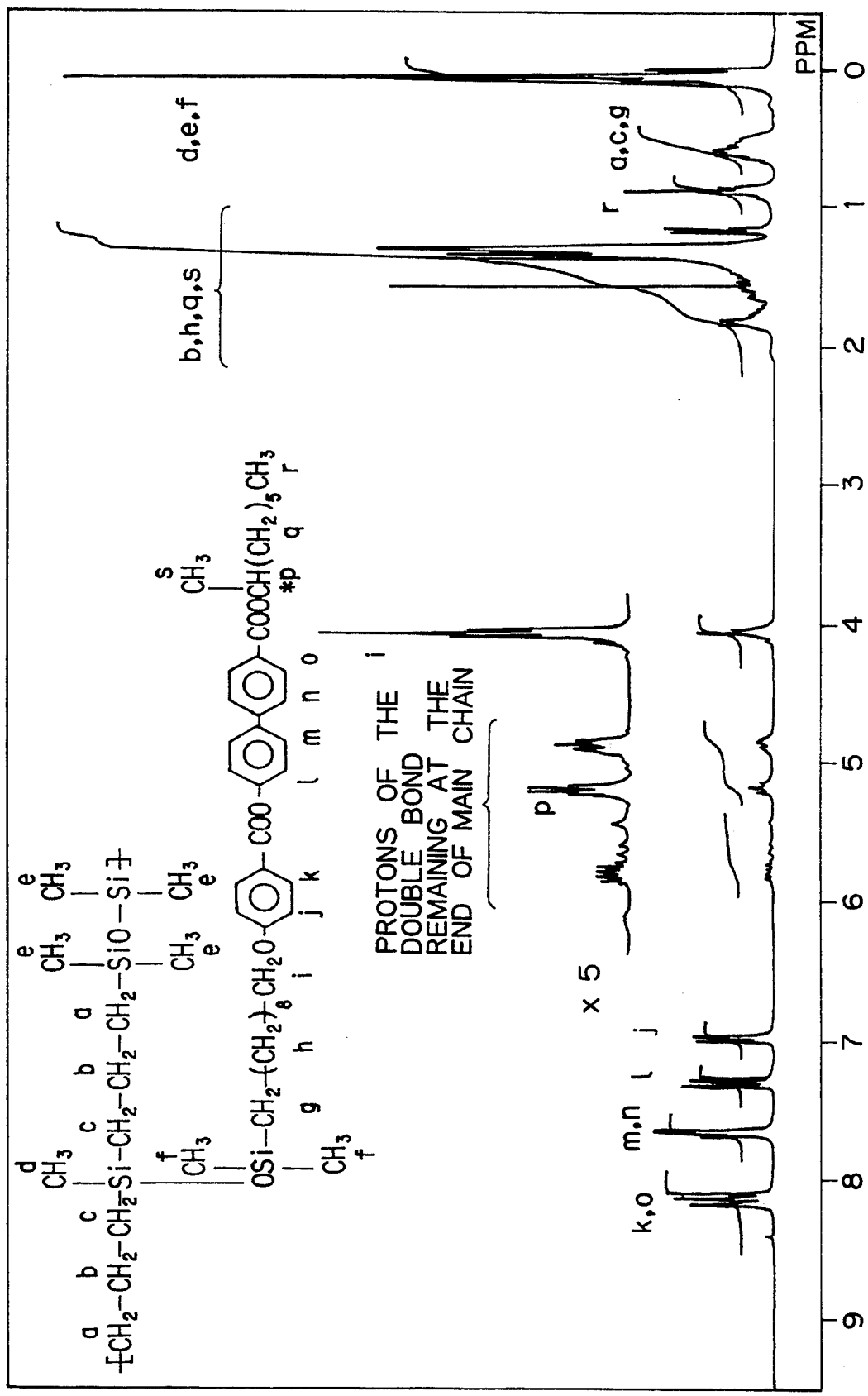
FIG. 6 is a $^1$H-NMR chart of high polymer C obtained in Example 3.

[3] Polymerization 0.30 g of monomer (b) was dissolved in 4 ml of toluene, and the atmosphere was replaced by argon. After the addition of 97 mg of 1,1,3,3-tetramethyldisiloxane and 40 μl of a 4% by weight 2-propanol solution of hydrogen hexachloroplatinate (IV) hexahydrate, reaction was carried out at 85° C. for 18 hours. After the solvent was distilled off under reduced pressure, the residue was purified by a silica gel column chromatography, to obtain 0.32 g of high polymer C (Yield: 81%). The $^1$H-NMR chart and properties of high polymer C are shown in FIG. 6 and Table 2, respectively.

EXAMPLE 4

Synthesis of high polymer D

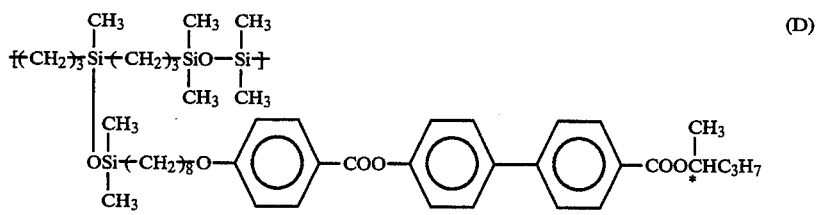

(D)

[1] Synthesis of methyl 4-(7-octenyloxy)benzoate (8)

5.2 g of 8-bromooctene, 5.0 g of methyl 4-hydroxybenzoate and 14 g of potassium carbonate were added to 70 ml of 2-butanone, and the mixture was refluxed for 7 hours in an atmosphere of argon. After the solid matters formed therein were filtered off, the solvent was distilled off under reduced pressure. The residue was purified by a silica gel column chromatography, to obtain 4.9 g of compound (8) (Yield: 68%)

[2] Synthesis of 4-(7-octenyloxy)benzoic acid (9)

4.9 g of compound (8) and 3.7 g of potassium hydroxide were added to a solvent mixture of 50 ml of water and 20 ml of methanol, and the mixture was refluxed for 5 hours. The reaction solution was poured to 200 ml water, and the mixture was adjusted approximately to pH 1 with concentrated hydrochloric acid. The solid matters formed therein were filtered, washed with water and dried, to obtain 4.0 g of compound (9) (Yield: 87%)

[3] Synthesis of compound (10)

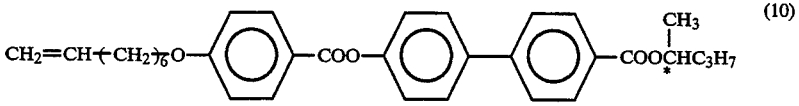

(10)

7 ml of thionyl chloride was added to 3.8 g of compound (9), and the mixture was stirred at 60° C. for three hours. After the excessive thionyl chloride was distilled off under reduced pressure, 10 ml of toluene was added. Thereto were added dropwise, at room temperature, a solution of 4.6 g of (S)-1-methylbutyl 4-hydroxybiphenyl-4'-carboxylate and 1.2 g of pyridine dissolved in 8 ml of toluene, and reaction was then carried out for a day at room temperature. The insoluble matters formed therein were filtered off, and the solvent was distilled off under reduced pressure. The residue was recrystallized from ethanol, to obtain 4.8 g of the objective compound (10) (Yield: 65%)

[4] Synthesis of monomer (c)

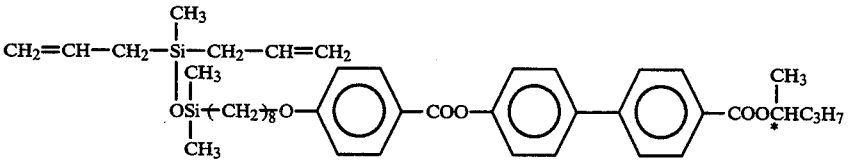

(c)

5.0 g of diallyldichlorosilane was dissolved in 35 ml of THF, and thereto was added dropwise 22 ml of a 1.4M diethyl ether solution of methyl lithium in an atmosphere of argon over a 10 minutes interval, during cooling with water. The mixture was then stirred for 5 hours during cooling with water. The solid matters formed therein were removed off, to obtain an ether solution of diallylchloromethylsilane (2).

At the same time, 4.7 g of compound (10) was dissolved in 10 ml of toluene, and thereto were added 2.5 g of chlorodimethylsilane and 70 μl of a 4% by weight 2-propanol solution of hydrogen hexachloroplatinate (IV) hexahydrate. The mixture was stirred at 100° C. for 5 hours in an atmosphere of argon, to obtain chlorosilane compound (11). The reaction solution was added to a solution mixture of 240 ml of THF and 16 ml of water, and the mixture was allowed to stand at room temperature for 10 minutes, to obtain silanol compound (12).

Figure 7:
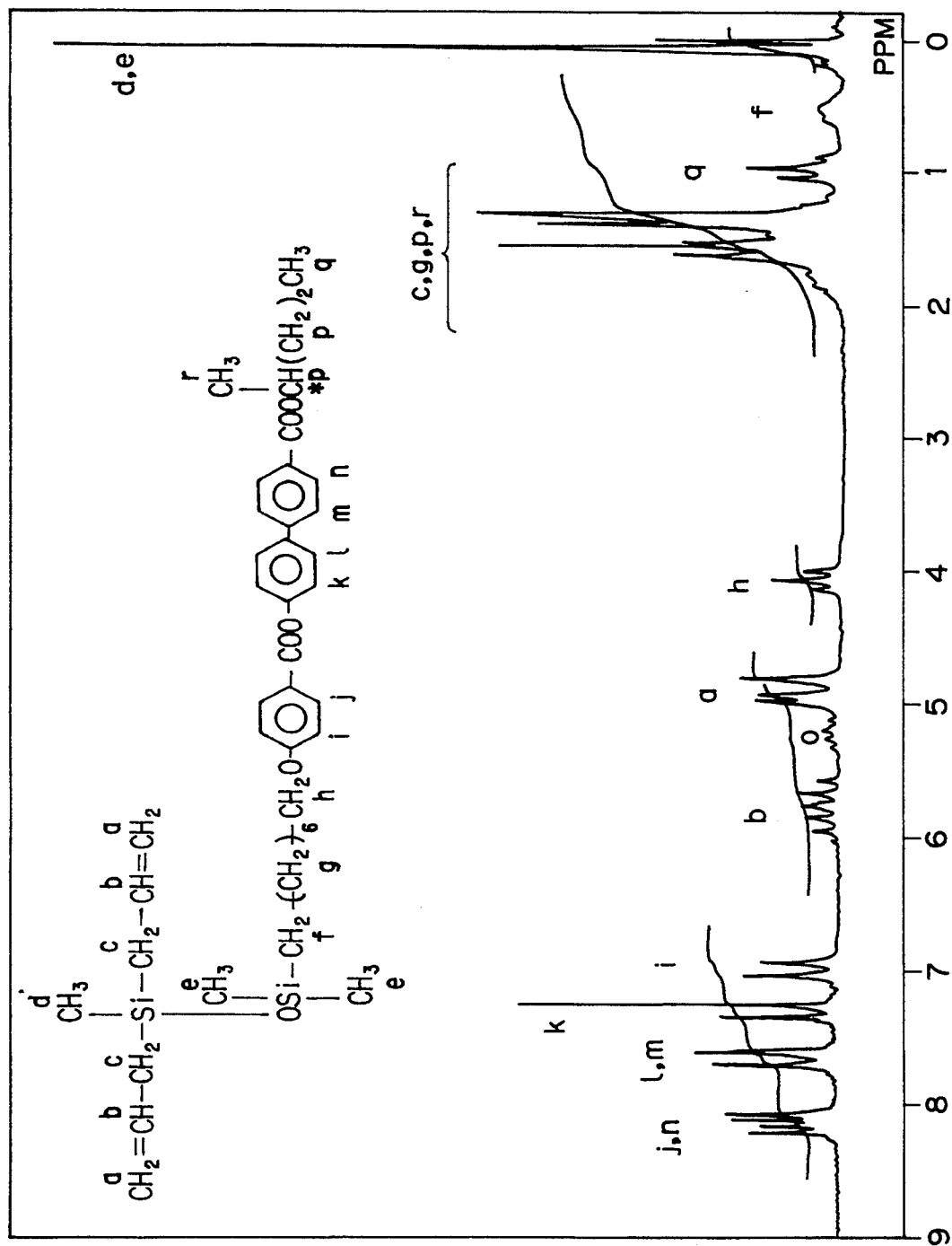
FIG. 7 is a $^1$H-NMR chart of monomer (c) obtained in Example 4.

After the reaction solution was dried over magnesium sulfate, thereto were added dropwise the above-described ether solution of diallylchloromethylsilane (2) and 2.2 g of triethylamine, in an atmosphere of argon during cooling with water. Reaction was then carried out for two days during cooling with water. After the solid matters formed therein were filtered off, the residue was washed with a saline solution and dried over magnesium sulfate, and the solvent was then distilled off under reduced pressure. The residue was purified by a silica gel column chromatography, to obtain 1.5 g of the objective monomer (c) (Yield: 22%). The ¹H-NMR chart and properties of monomer (c) are shown in FIG. 7 and Table 1, respectively.

Figure 8:
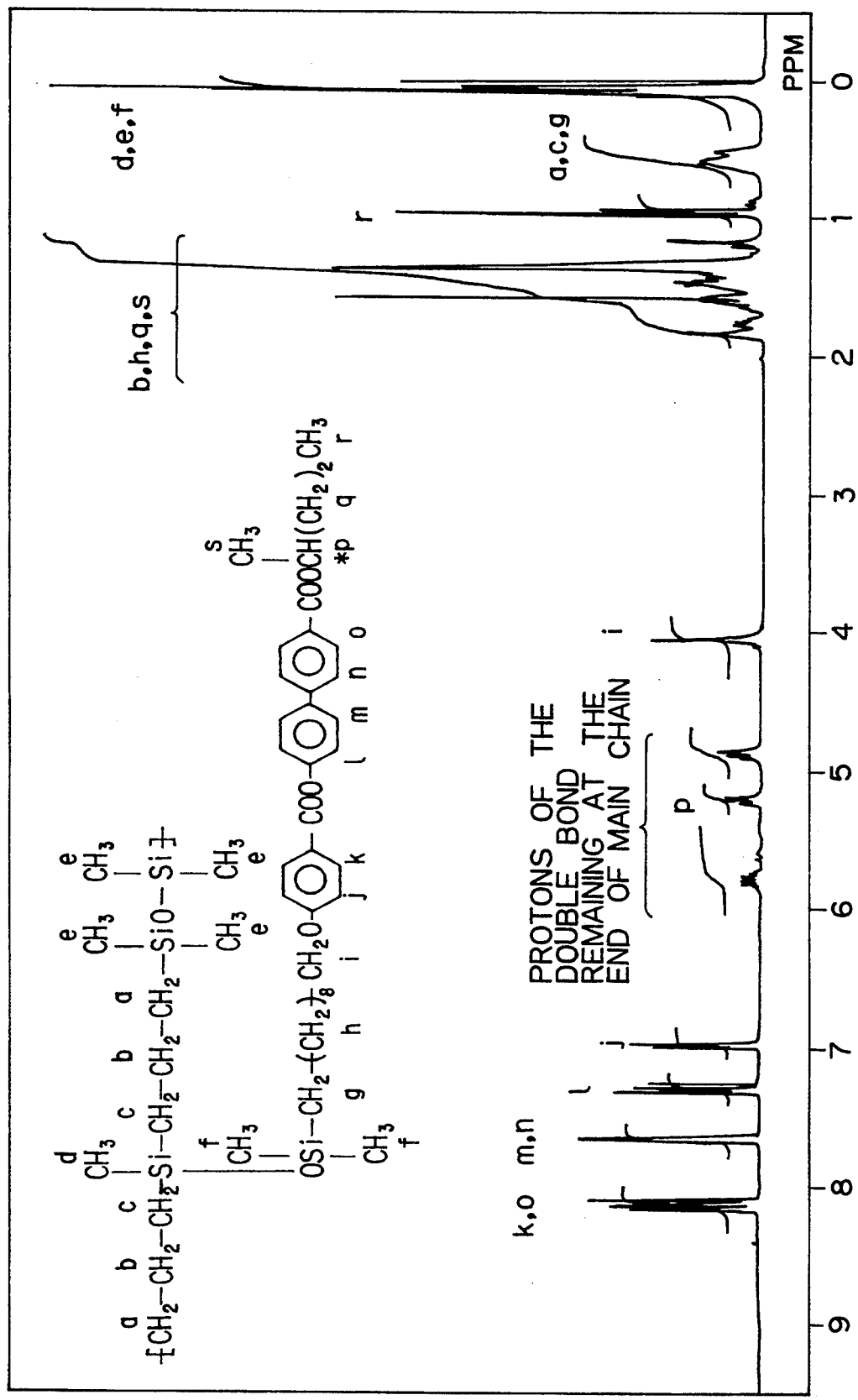
FIG. 8 is a $^1$H-NMR chart of high polymer D obtained in Example 4.

[5] Polymerization 0.40 g of monomer (c) was dissolved in 5 ml of toluene, and the atmosphere was replaced argon. After the addition of 0.12 g of 1,1,3,3-tetramethyldisiloxane and 40 μl of a 4% by weight 2-propanol solution of hydrogen hexachloroplatinate (IV) hexahydrate, reaction was carried out at 85° C. for 17 hours. After the solvent was distilled off under reduced pressure, the residue was purified by a silica gel column chromatography, to obtain 0.42 g of high polymer D (Yield: 81%). The ¹H-NMR chart and properties of high polymer D are shown in FIG. 8 and Table 2, respectively.

EXAMPLE 5

Synthesis of high polymer E

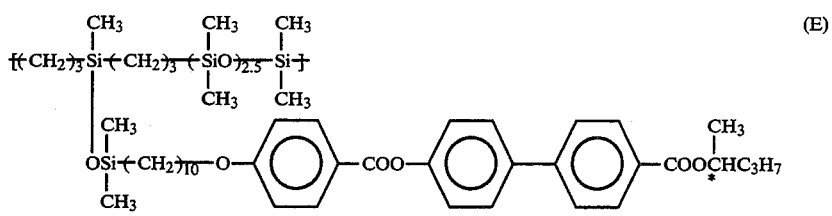

Figure 9:
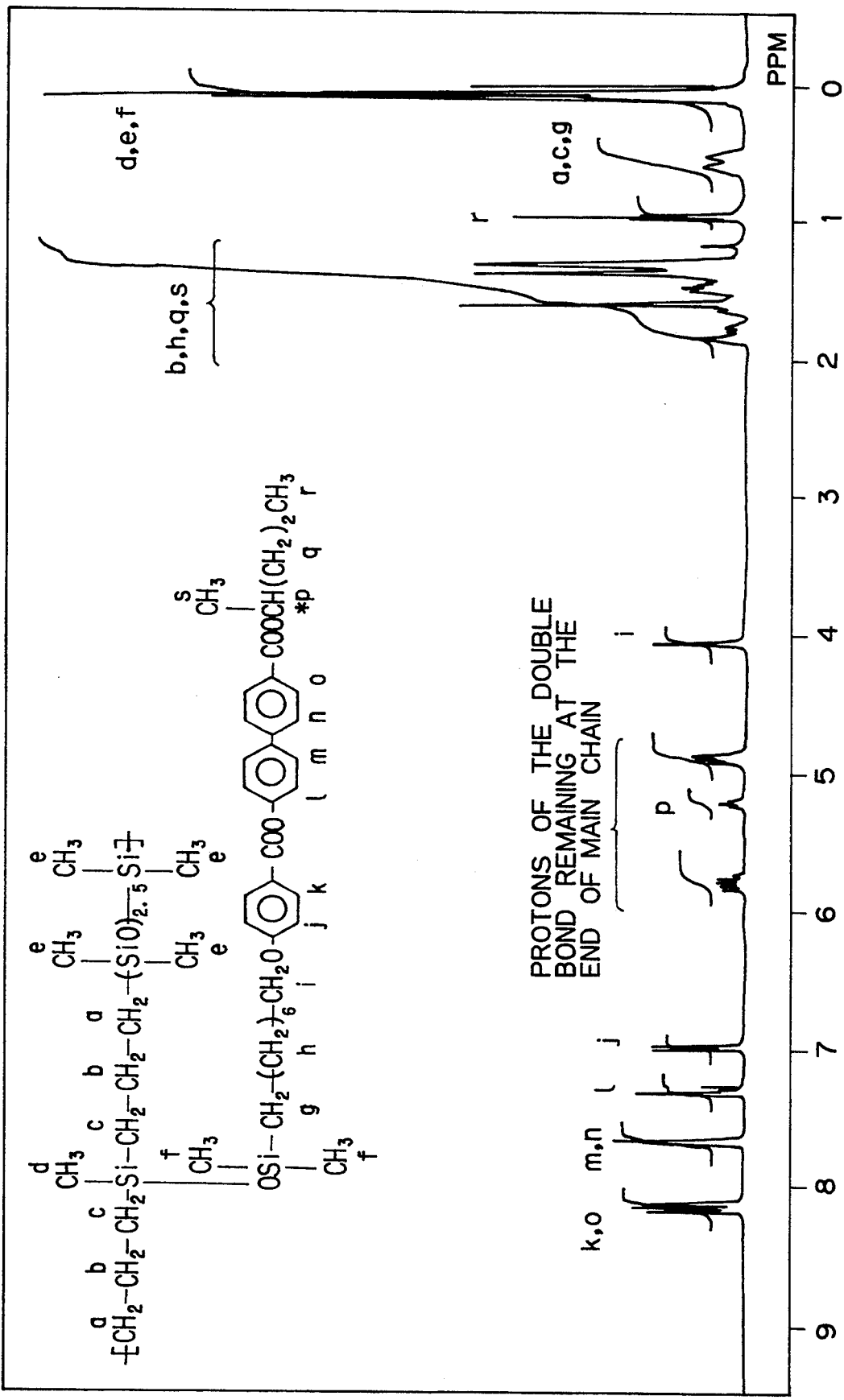
FIG. 9 is a $^1$H-NMR chart of high polymer E obtained in Example 5.

0.10 g of monomer (a) obtained in the same manner as in Example 1 was dissolved in 2 ml of toluene, and the atmosphere was replaced by argon. After the addition of 97 mg of an α,ω-hydrogen-oligodimethylsiloxane (weight average molecular weight: 670) and 20 μl of a 4% by weight 2-propanol solution of hydrogen hexachloroplatinate (IV) hexahydrate, reaction was carried out at 85° C. for 15 hours. Thereto were further added 0.40 g of monomer (a), 48 mg of 1,1,3,3-tetramethyldisiloxane, 10 μl of a 4% by weight 2-propanol solution of hydrogen hexachloroplatinate (IV) hexahydrate and 2 ml of toluene, and reaction was carried out at 85° C. for four hours. After the solvent was distilled off under reduced pressure, the residue was purified by a silica gel column chromatography, to obtain 0.52 g of high polymer E (Yield: 81%). The 1H-NMR chart and properties of high polymer E are shown in FIG. 9 and Table 2, respectively.

EXAMPLE 6

Synthesis of high polymer F

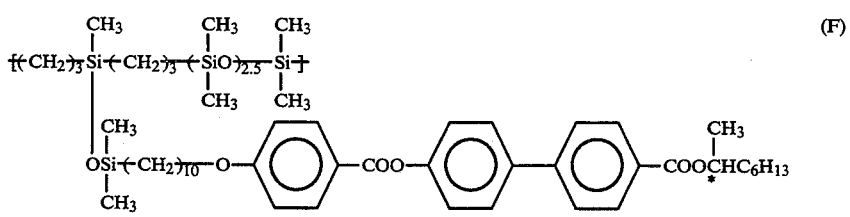

Figure 10:
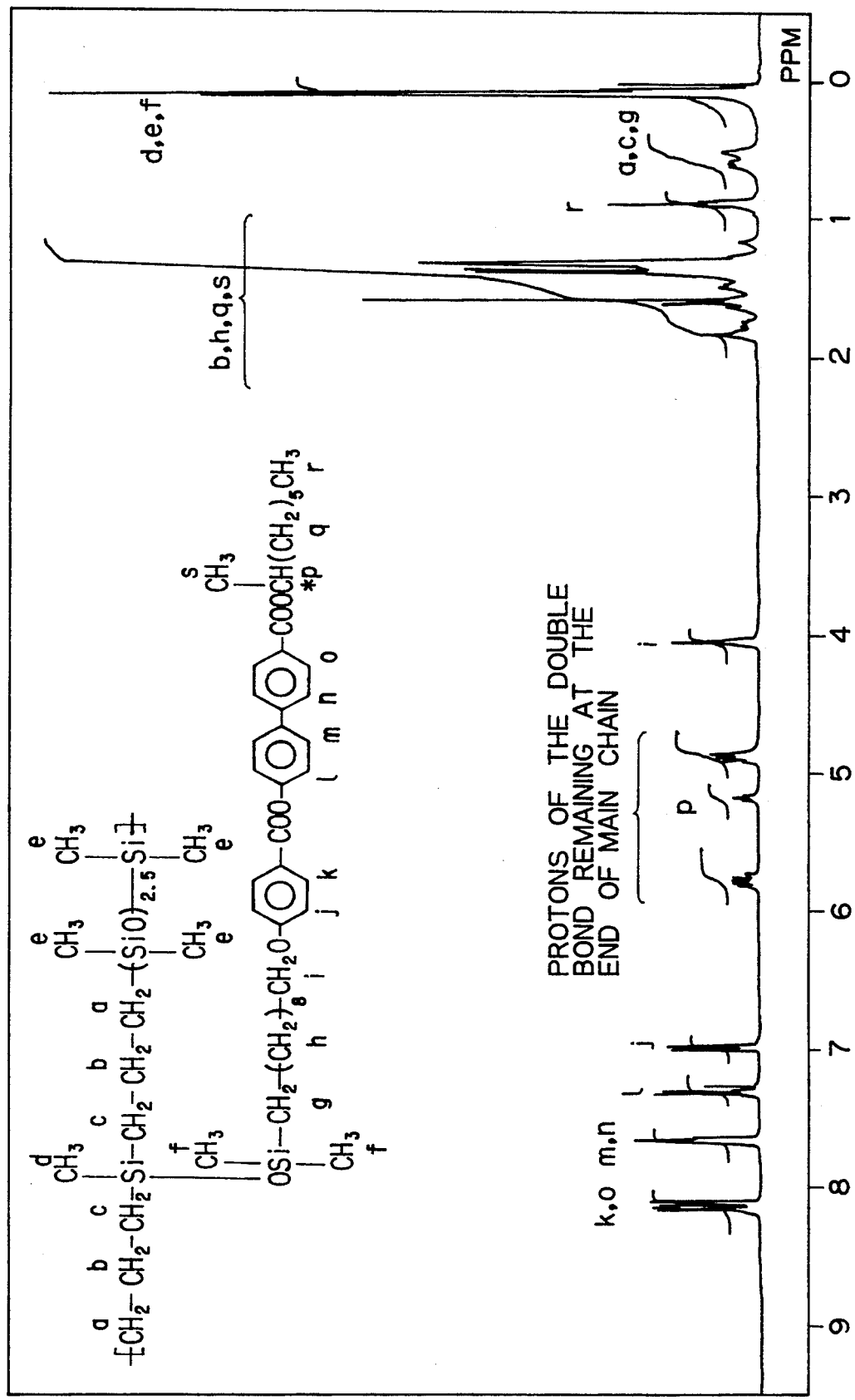
FIG. 10 is a $^1$H-NMR chart of high polymer F obtained in Example 6.

80 mg of monomer (b) obtained in the same manner as that of Example 3 was dissolved in 2 ml of toluene, and the atmosphere was replaced by argon. After the addition of 70 mg of an α,ω-hydrogen-oligodimethylsiloxane (weight average molecular weight: 670) and 20 μl of a 4% by weight 2-propanol solution of hydrogen hexachloroplatinate (IV) hexahydrate, reaction was carried out at 85° C. for 15 hours. After Further addition of 0.32 g of monomer (b), 36 mg of 1,1,3,3-tetramethyldisiloxane, 10 μl of a 4% by weight 2-propanol solution of hydrogen hexachloroplatinate (IV) hexahydrate and 2 ml of toluene, reaction was carried out at 85° C. for hours. The solvent was distilled off under reduced pressure, and the residue was purified by a silica gel column chromatography, to obtain 0.43 g of high polymer F (Yield: 85%). The 1H-NMR chart and properties of high polymer F are shown in FIG. 10 and Table 2, respectively.

EXAMPLE 7

Synthesis of high polymer G

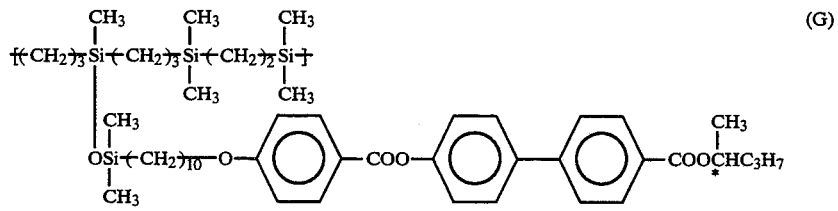

0.40 g of monomer (a) was dissolved in 4 ml of toluene, and the atmosphere was replaced by argon. After the addition of 44 mg of 1,1,4,4-tetramethyldisilethylene and 20 μl of a 4% by weight 2-propanol solution of hydrogen hexachloroplatinate (IV) hexahydrate, reaction was carried out at 85° C. for three hours. After the solvent was distilled off under reduced pressure, the residue was purified by a silica gel column chromatography, to obtain 0.39 g of high polymer G (Yield: 88%).

Figure 11:
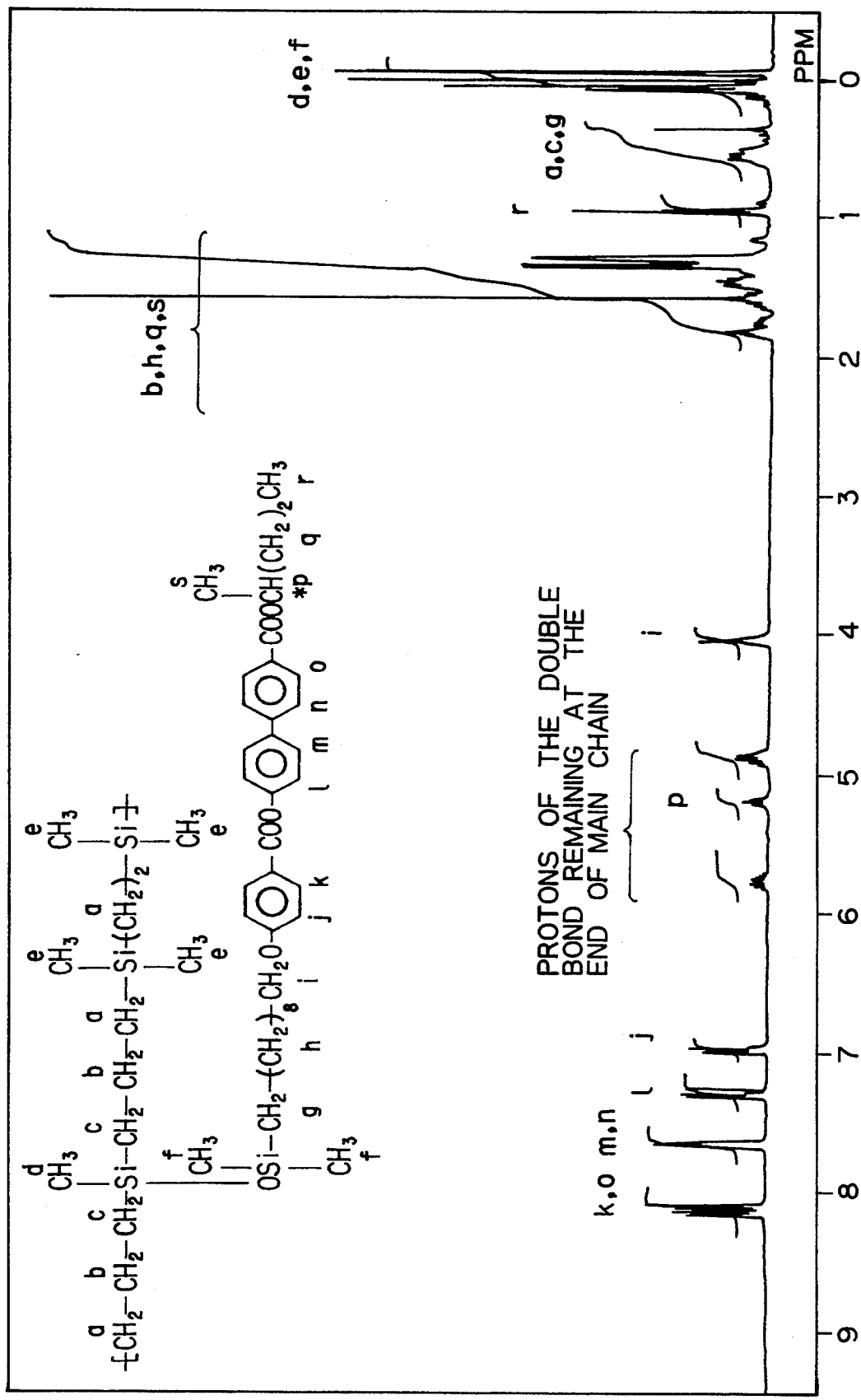
FIG. 11 is a $^1$H-NMR chart of high polymer G obtained in Example 7.

The 1H-NMR chart and properties of high polymer G are shown in FIG. 11 and Table 2, respectively.

EXAMPLE 8

Synthesis of high polymer H

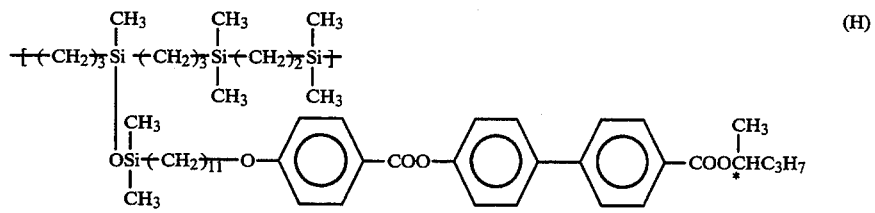

[1] Synthesis of compound (13)

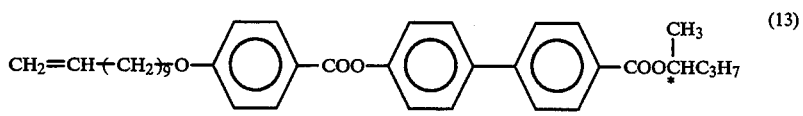

3 ml of chloride was added to 4.0 g of 4-(10-undecenyloxy)benzoic acid, and the mixture was stirred at 70° C. for four hours. After the excessive thionyl chloride was distilled off under reduced pressure, 30 ml of toluene was added. Thereto were added dropwise, at room temperature, a solution of 3.7 g of (s)-1-methylbutyl 4-hydroxybiphenyl-4'-carboxylate and 1.3 g of pyridine dissolved in 15 ml of toluene, and reaction was carried out for a day at room temperature. The insoluble matters formed therein were filtered off, and the solvent was distilled off under reduced pressure. The residue was recrystallized from ethanol, to obtain 4.3 g of the objective compound (13) (Yield: 55%).

[2] Synthesis of monomer (d)

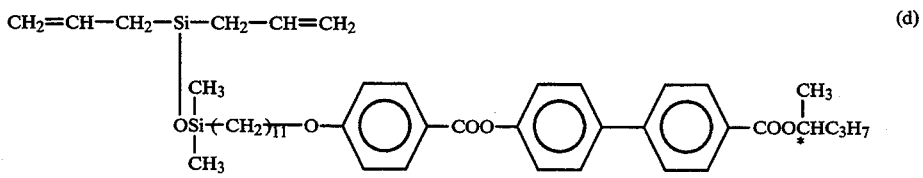

2.6 g of diallyldichlorosilane was dissolved in 40 ml of THF, and thereto was added dropwise 10 ml of a 1.4M diethyl ether solution of methyl lithium, in an atmosphere of argon during cooling with water. The mixture was then stirred for three hours during cooling with water. The solid matters formed therein were removed off, to obtain an ether solution of diallylchloromethylsilane (2).

At the same time, 4.0 g of compound (13) was dissolved in 8 ml of toluene, and thereto were added 1.4 g of chlorodimethylsilane and 80 μl of a 4% by weight 2-propanol solution of hydrogen hexachloroplatinate (IV) hexahydrate. The mixture was then stirred at 100° C. for 3.5 hours in an atmosphere of argon, to obtain chlorosilane compound (14). To the reaction solution were added a solution of 0.13 g of water and 0.73 g of triethylamine dissolved in 40 ml of THF, and the mixture was stirred for 10 minutes during cooling with water, to obtain silanol compound (15).

Figure 12:
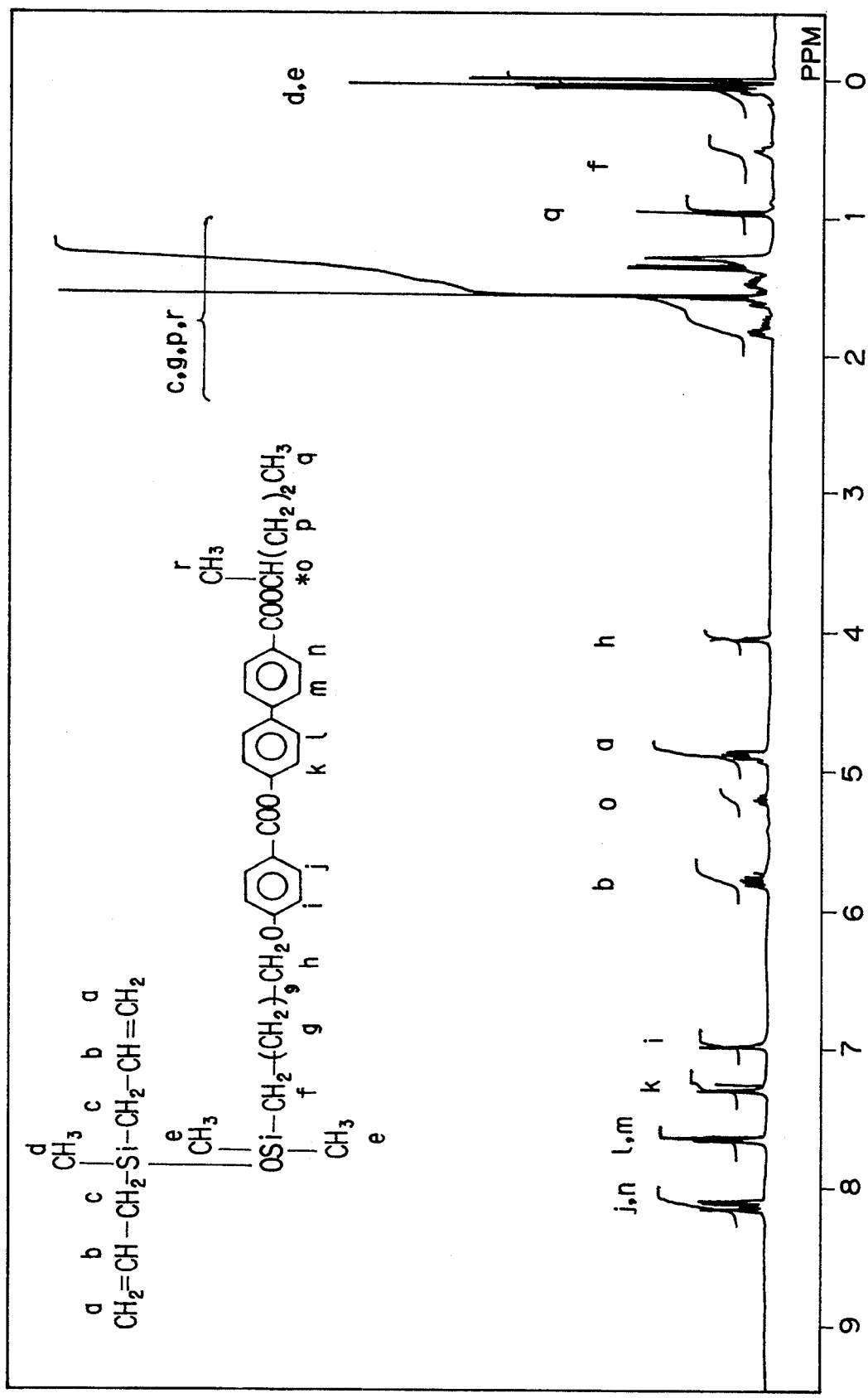
FIG. 12 is a $^1$H-NMR chart of monomer (d) obtained in Example 8.

To the reaction solution were added dropwise the above-described ether solution of diallylchloromethylsilane (2) and a solution of 1.5 g of triethylamine dissolved in 40 ml of THF, in an atmosphere of argon during cooling with water. Reaction was then carried out at room temperature for two days. The reaction solution was then washed with a saline solution and dried over magnesium sulfate, and the solvent was distilled off under reduced pressure. After a purification by a silica gel column chromatography, the residue was recrystallized from ethanol, to obtain 1.5 g of the objective monomer (d) (Yield: 28%). The $^1$H-NMR chart and properties of monomer (d) are shown in FIG. 12 and Table 1, respectively.

Figure 13:
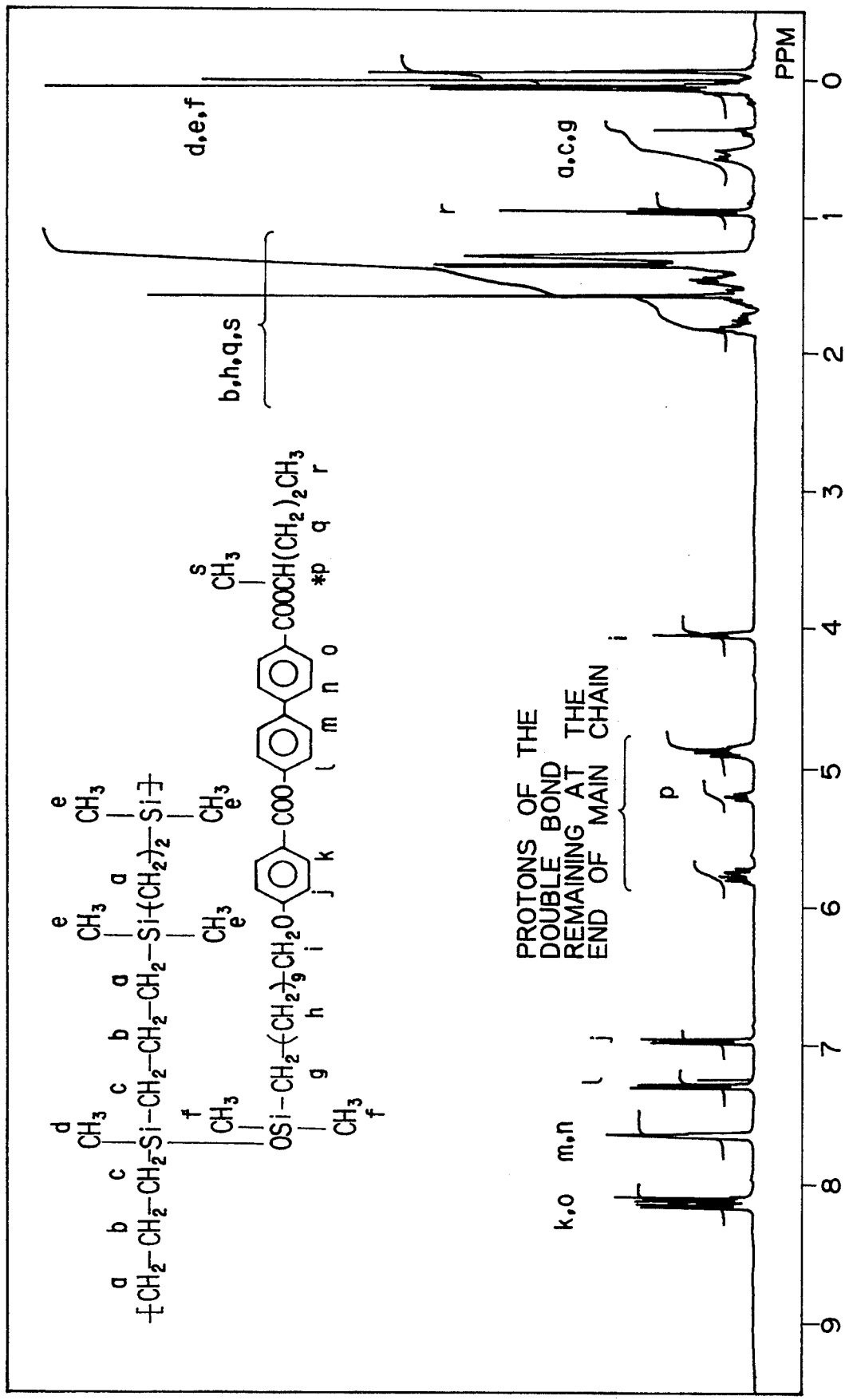
FIG. 13 is a $^1$H-NMR chart of high polymer H obtained in Example 8.

[3] Polymerization 0.29 g of monomer (d) was dissolved in 4 ml of toluene, and the atmosphere was replaced by argon. After the addition of 24 mg of 1,1,4,4-tetramethyldisilethylene and 20 μl of a 4% by weight 2-propanol solution of hydrogen hexachloroplatinate (IV) hexahydrate, reaction was carried out at 85° C. for three hours. After the solvent was distilled off under reduced pressure, the residue was purified by a silica gel column chromatography, to obtain 0.32 g of high polymer II (Yield: 92%). The $^1$H-NMR chart and properties of the high polymer H are shown in FIG. 13 and Table 2, respectively.

EXAMPLE 9

Synthesis of high polymer I

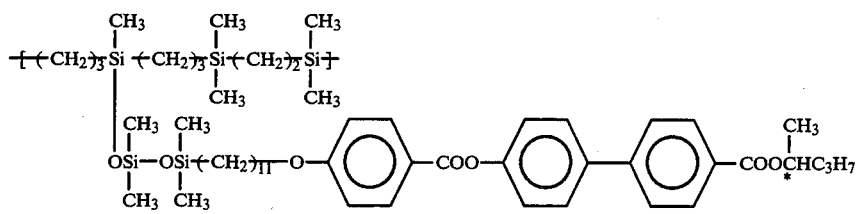

(I)

[1] Synthesis of monomer (e)

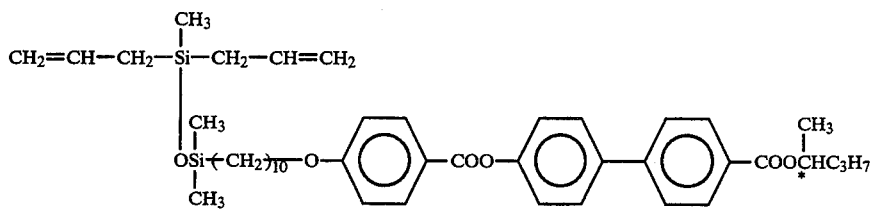

(e)

5.2 g of diallyldichlorosilane was dissolved in 40 ml of THF, and thereto was added dropwise 20 ml of a 1.4M diethyl ether solution of methyl lithium, in an atmosphere of argon during cooling with water. The mixture was then stirred for two hours during cooling with water. The solid matters formed therein were removed off, to obtain an ether solution of diallylchloromethylsilane (2). Thereto were added 0.52 g of water and a solution of 2.9 g of triethylamine dissolved in 50 ml of THF, and the mixture was then stirred for 10 minutes in an atmosphere of argon, to obtain an ether solution of silanol compound (16).

Figure 14:
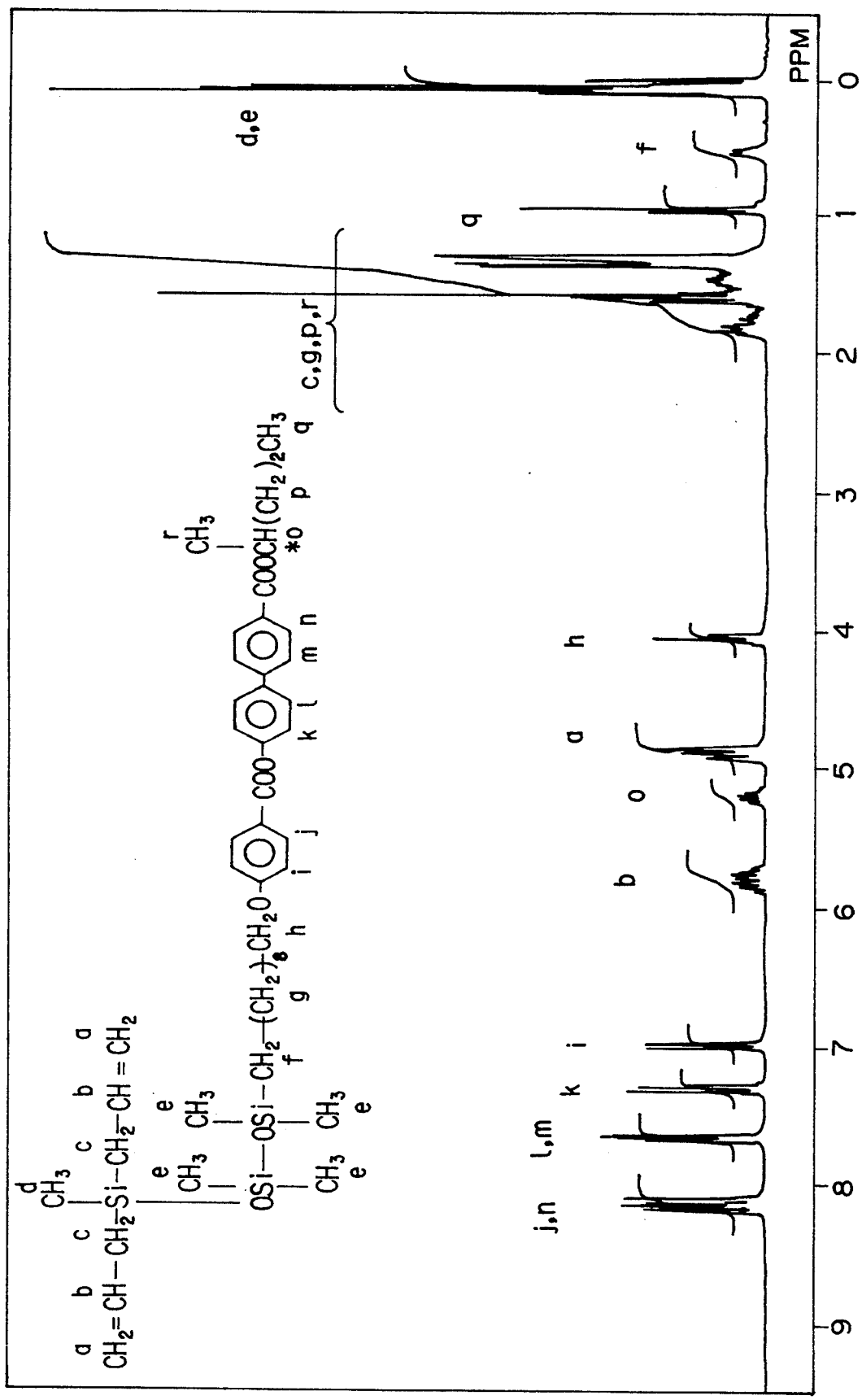
FIG. 14 is a $^1$H-NMR chart of monomer (e) obtained is in Example 9.

At the same time, 5.2 g of compound (1) was dissolved in 10 ml of toluene, and thereto were added 1.8 g of chlorodimethylsilane and 50 μl of a 4% by weight 2-propanol solution of hydrogen hexachloroplatinate (IV) hexahydrate. The mixture was stirred at 100° C. for 2.5 hours in an atmosphere of argon, to obtain chlorosilane compound (2). To the reaction solution were added a solution of 0.17 g of water and 0.96 g of triethylamine dissolved in 50 ml of THF, and the mixture was then stirred For 10 minutes during cooling with water, to obtain silanol compound (3). The reaction solution and the above-described ether solution of silanol compound (16) were mixed, and to the mixture were added dropwise a solution of 3.9 g of triethylamine dissolved in 50 ml of THF and a solution of 2.5 g of dichlorodimethylsilane dissolved in 50 ml of THF, in an atmosphere of argon during cooling with water. Reaction was then carried out at room temperature for two days. The reaction solution was washed with a saline solution and dried over magnesium sulfate, and the solvent was then distilled off under reduced pressure. After a purification by a silica gel column chromatography, the residue was recrystallized from ethanol, to obtain 2.5 g of the objective monomer (e) (Yield: 32%). The $^1$H-NMR chart and properties of monomer (e) are shown in FIG. 14 and Table 1, respectively.

[2] Polymerization 0.20 g of monomer (e) was dissolved in 3 ml of toluene, and the atmosphere was replaced by argon. After the addition of 16 mg of 1,1,4,4-tetramethyldisilethylene and 15 μl of a 4% by weight 2-propanol solution of hydrogen hexachloroplatinate (IV) hexahydrate, reaction was carried out at 85° C. for three hours. After the solvent was distilled off under reduced pressure, the residue was purified by a silica gel column chromatography, to obtain 0.21 g of high polymer I (Yield: 97%).

Figure 15:
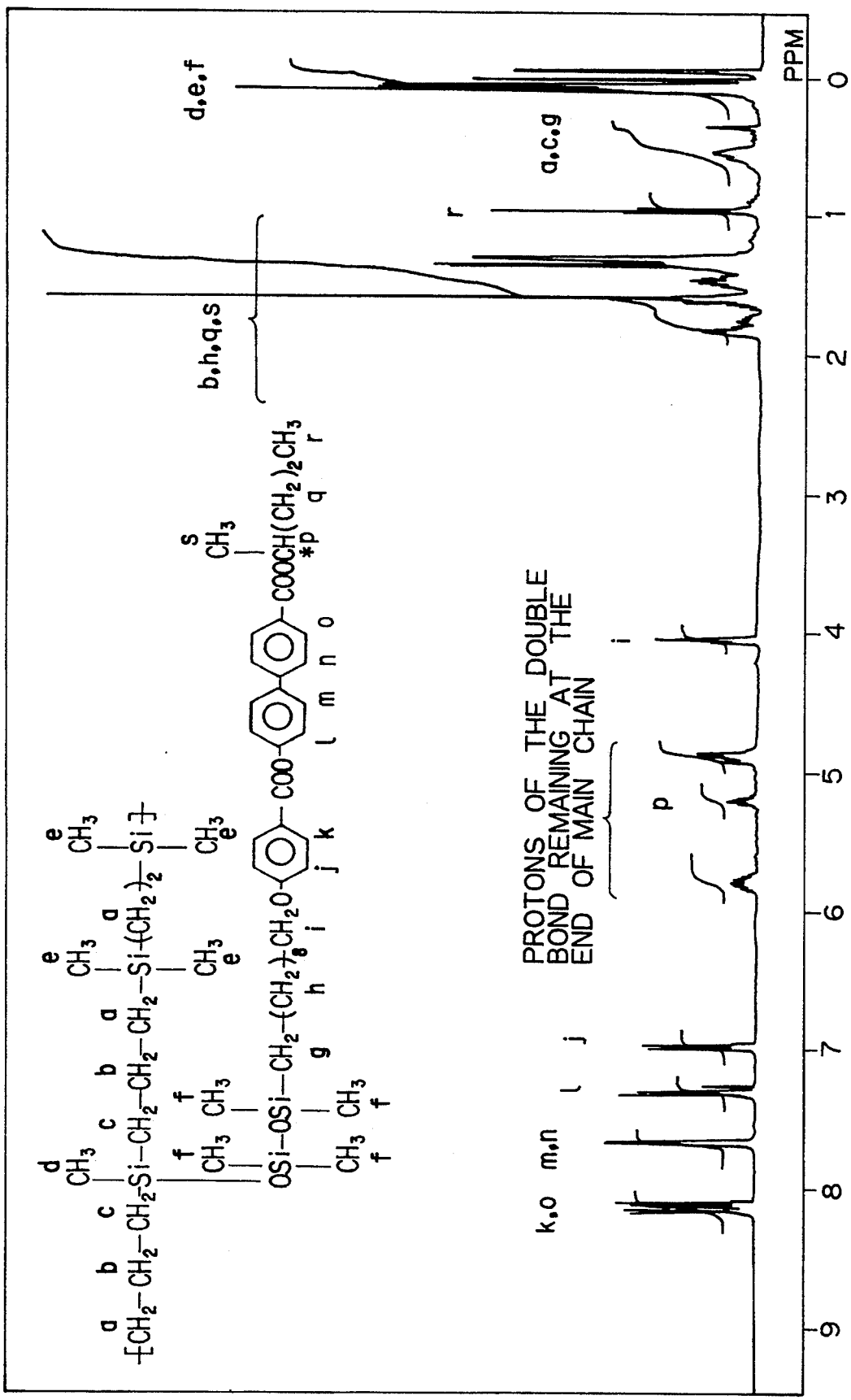
FIG. 15 is a $^1$H-NMR chart of high polymer I obtained in Example 9.

The $^1$H-NMR chart and properties of high polymer I are shown in FIG. 15 and Table 2, respectively.

EXAMPLE 10

Synthesis of monomer (a)

[1] Synthesis of bromo-compound (17)

5.8 g of diallyldichlorosilane was dissolved in 20 ml of THF, and thereto was added dropwise 23 ml of a 1.4M diethyl ether solution of methyl lithium, in an atmosphere of argon during cooling with water. The mixture was then stirred for two hours, during cooling with water. The solid matters formed therein were removed off, to obtain an ether solution of diallylchloromethylsilane (2).

At the same time, 4.0 g of 4-(9-decenyloxy)bromobenzene (18) was dissolved in 8 ml of toluene, and thereto were added 2.4 g of chlorodimethylsilane and 140 μl of a 4% by weight 2-propanol solution of hydrogen hexachloroplatinate (IV) hexahydrate. The mixture was then stirred for 3.5 hours at 100° C. in an atmosphere of argon, to obtain chlorosilane compound (19). To the reaction solution were added a solution of 0.26 g of water and 1.4 g of triethylamine dissolved in 40 ml of THF, and the mixture was stirred for 10 minutes during cooling with water, to obtain silanol compound (20).

To the reaction solution were added dropwise the above-described ether solution of diallylchloromethylsilane (2) and a solution of 3.3 g of triethylamine dissolved in 40 ml of THF, in an atmosphere of argon, during cooling with water. The reaction solution was washed with a saline solution and dried over magnesium sulfate, and the solvent was then distilled off under reduced pressure. The residue was purified by a silica gel column chromatography, to obtain 3.2 g of the objective bromo-compound (17) (Yield: 49%).

[2] Synthesis of monomer (a)

1.0 g of bromo-compound (17), 71 mg of magnesium and 42 mg of 1,2-dibromoethane were added to 40 ml of THF, and the mixture was refluxed for 5 hours. The mixture was then added to 33 g of dry ice and was then allowed to stand to be brought back to room temperature, and methylene chloride was added thereto. The mixture was then washed with a 2N hydrochloric acid and a saline solution and was dried over magnesium sulfate, and the solvent was then distilled off under reduced pressure, to obtain carboxylic acid (21).

0.7 g of the compound (21), 0.42 g of (s)-1-methylbutyl 4-hydroxybiphenyl-4'-carboxylate, 0.33 g of DCC and 36 mg of 4-dimethylaminopyridine were dissolved in 10 ml of toluene, and the mixture was stirred at room temperature for 8 hours. After the precipitates in the mixture were removed off, the solvent was distilled off under reduced pressure. The residue was purified by a silica gel column chromatography and was then recrystallized from ethanol to obtain 0.56 g of the objective monomer (a) (Yield from bromo-compound: 38%). From the $^1$H-NMR chart and the results of the measurement of phase transition temperatures of the monomer (a), the monomer (a) obtained in Example 10 was confirmed to be identical with the monomer (a) obtained in Example 1

TABLE 1

| Monomer | Phase Transition Behavior/°C. | Response Time μs |
|---|---|---|
| a | glass ⇐$_{-23}$ S$_C$* ⇐$_{78}$ Iso | 66 |
| b | glass ⇐$_{5}$ S$_C$* ⇐$_{49}$ Iso | 84 |
| c | glass ⇐$_{-5}$ S$_C$* ⇐$_{62}$ Iso | 67 |
| d | glass ⇐$_{-25}$ S$_C$* ⇐$_{81}$ Iso | 84 |
| e | glass ⇐$_{-27}$ S$_C$* ⇐$_{74}$ Iso | 82 |

TABLE 2

| High Polymer | Phase Transition Behavior/°C. | Mw | Response Time ms |
|---|---|---|---|
| A | glass ⇐$_{-25}$ S$_C$* ⇐$_{73}$ Iso | 3500 | 2.3 |
| B | glass ⇐$_{-27}$ S$_C$* ⇐$_{40}$ Iso | 3000 | 1.5 |
| C | glass ⇐$_{-11}$ S$_C$* ⇐$_{49}$ Iso | 3000 | 1.0 |
| D | glass ⇐$_{-18}$ S$_C$* ⇐$_{45}$ Iso | 2500 | 1.0 |
| E | glass ⇐$_{-22}$ S$_C$* ⇐$_{52}$ Iso | 3600 | 0.93 |
| F | glass ⇐$_{0}$ Iso | 3300 | — |
| G | glass ⇐$_{-20}$ S$_C$* ⇐$_{83}$ Iso | 3700 | 2.8 |
| H | glass ⇐$_{-20}$ S$_C$* ⇐$_{82}$ Iso | 3100 | 1.5 |
| I | glass ⇐$_{-25}$ S$_C$* ⇐$_{69}$ Iso | 3500 | 0.74 |

EXAMPLE 11

A composition was prepared by mixing high polymer D obtained in Example 4 and a ferroelectric liquid crystal CS-1015 (Trade name, produced by Chisso Sekiyukagaku Kabushiki Kaisha) in a weight ratio of 8:2.

Phase transition behavior of CS-1015

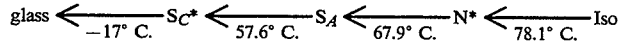

Mixing method 40 mg of high polymer D obtained in Example 4 and 10 mg of CS-1015 were dissolved in 5 ml of a solvent (dichloromethane), and the solution was stirred sufficiently. The solvent was then evaporated at about 100° C.

The composition was disposed between two glass substrates with ITO electrodes (electrode area: 0.2 cm$^2$, thickness of ITO: 1000 angstroms) (cell thickness: 3 μm), and was observed by using a polarizing microscope with a magnification of x400 to identify phases. A voltage of ±10 V was applied between the electrodes, according to demand.

Phase transition behavior of the composition

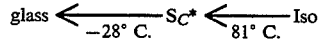

In the liquid crystal state of the composition, there was not observed the island structure peculiar to dispersion systems but was observed uniform liquid crystal phases whereby the compatibility of the high polymer with the other liquid crystal was confirmed. The composition in the cell was then oriented by applying shear stress between the substrates several times at 79° C. (orientation by a shearing method). When a rectangular voltage of ±30 V was applied between the substrates at 25° C., the response time was measured to be 0.46 ms.

EXAMPLE 12

A composition was prepared by mixing high polymer A obtained in Example 1 and the following liquid crystal P1008 (Trade name: produced by Midori Kagaku Kabushiki Kaisha) in a weight ratio of 8:2.

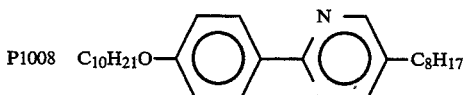

Phase transition behavior

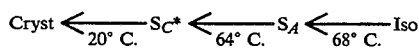

The mixing method was the same as that of Example 11.
Phase transition behavior of the composition

Response time at 25° C.: 0.63 ms

The methods and conditions employed for the measurements of phase transition behavior and response time were the same as in Example 11, with the exception that the orientation temperature was 87° C.

In the liquid crystal state of the composition, there was not observed the island structure peculiar to dispersion systems but was observed uniform liquid crystal phases whereby the compatibility of the high polymer with the other liquid crystal was confirmed.

EXAMPLE 13

A composition was prepared by mixing high polymer F obtained in Example 6 and a liquid crystal P1008 in a weight ratio of 8:2. The mixing method was the same as that of Example 11.

Phase transition behavior of the composition

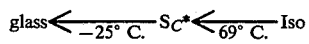

Response time at 25° C.: 0.23 ms

The methods and conditions employed for the measurements of phase transition behavior and response time were the same as in Example 11, with the exception that the orientation temperature was 67° C.

In the liquid crystal state of the composition, there was not observed the island structure peculiar to dispersion systems but was observed uniform liquid crystal phases whereby the compatibility of the high polymer with the other liquid crystal was confirmed.

EXAMPLE 14

Compositions were prepared by mixing high polymer B obtained in Example 2 and the following low molecular weight liquid crystal, which is a known one and was synthesized by a common method, in weight ratios listed in Table 3.

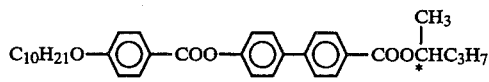

Phase transition behavior

$S_x^{}$ is a smectic phase of a higher degree than that of $S_C^{}$.

The mixing method was the same as that of Example 11. The methods for measuring phase transition behavior and response time were the same as those used in Example 11, with the proviso that the orientation temperature for the composition with the ratio of 8:2 was 106° C., and that for the one with the ratio of 6:4 was 121° C.

EXAMPLE 15

A liquid crystal optical device was produced by using the same liquid-crystalline composition as that prepared in Example 12. A 20% by weight toluene solution of the composition was applied to a thickness of 3 μm on the electroded surface of a polyethersulfon (PES) substrate provided with ITO electrode. Immediately after the solvent was dried off, a non-coated substrate of the same type was laminated on the coated substrate so that the liquid crystal layer came into contact with the electroded surfaces, to produce a sheet of unoriented liquid crystal device (width: 150 mm, length: 3 m).

Figure 16:
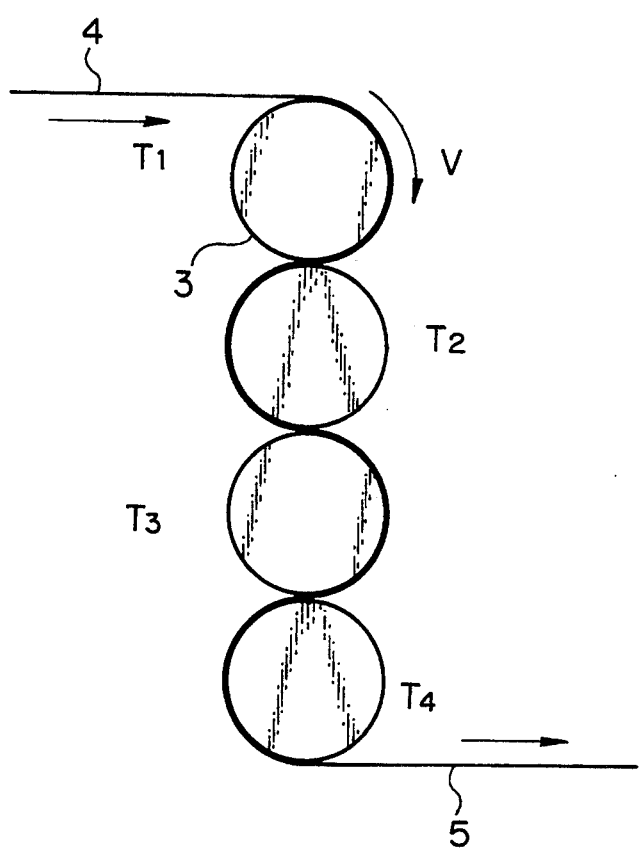
FIG. 16 is a schematic view illustrating the apparatus for orientation used in Examples.

Subsequently, the unoriented liquid crystal device 4 was oriented by a bending treatment using an orientation apparatus as shown in FIG. 16 which comprised four heated rolls. Each heated roll 3 was a chromium-plated iron roll of 80 mm in diameter and 300 mm in length. The surfaces of the rolls were adjusted to $T_1=90°$ C., $T_2=88°$ C., $T_3=86°$ C. and $T_4=82°$ C., and the line velocity to v=8 m/min. By using this apparatus, the liquid-crystalline composition in the unoriented liquid crystal device 4 cooled from the isotropic phase to a liquid crystal phase while being applied with shear by bending, to provide an oriented liquid crystal device 5, wherein the liquid-crystalline composition was uniaxially and homogeneously oriented in a direction perpendicular to the machine direction of the substrates.

Two polarizing plates were arranged over and below the oriented liquid crystal device so that their optical axes intersected at right angles. When a voltage of ±20 V was applied between the electrodes, a good contrast of 22 in contrast ratio was attained.

It was proved from the result that the composition was suitable for the continuous production of liquid crystal optical devices by using the above-described simple method.

EXAMPLE 16

A composition was prepared by mixing the high polymer G obtained in Example 7 and a liquid crystal P1008 in a weight ratio of 8:2. The mixing method was the same as that employed in Example 11. The phase transition behavior and response time of the obtained liquid-crystalline composition were as follows.

Phase transition behavior

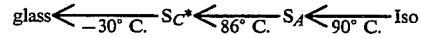

Response time at 25° C.: 0.69 ms

The methods and conditions employed for the measurements of phase transition behavior and response time were the same as those employed in Example 11, with the proviso that the orientation temperature was 88° C.

TABLE 3

| P-B:LLC | Phase Transition Behavior/°C. | Response Time (25° C.) |
|---|---|---|
| 8:2 (weight ratio) | glass $\underset{-25°\,C.}{\leftarrows}$ $S_C^*$ $\underset{100°\,C.}{\leftarrows}$ $S_A$ $\underset{108°\,C.}{\leftarrows}$ Iso | 0.68 ms |
| 6:4 (weight ratio) | Cryst $\underset{-25°\,C.}{\leftarrows}$ $S_C^*$ $\underset{96°\,C.}{\leftarrows}$ $S_A$ $\underset{108°\,C.}{\leftarrows}$ Iso | 0.55 ms |

P-B: the high polymer of Example 2
LLC: low molecular weight liquid crystal

In the liquid crystal state of the composition, there was not observed the island structure peculiar to dispersion systems but was observed uniform liquid crystal phases whereby the compatibility of the high polymer with the other liquid crystal was confirmed.

EXAMPLE 17

The high polymer G obtained in Example 7, the following high polymer J and a liquid crystal P1008 were mixed in a weight ratio of 5:2:3.

$$\text{(J)} \quad \{\!\!-\!(CH_2)_3CH\!-\!(CH_2)_3SiO\!-\!Si\!-\!\}$$ with CH₃ groups and pendant $-O-(CH_2)_{10}-O-\text{Ar}-COO-\text{Ar}-\text{Ar}-COOCH^*(CH_2)_2CH_3$ Phase transition behavior $$\text{glass} \underset{-10^\circ C}{\longleftrightarrow} S_C^* \underset{103^\circ C}{\longleftrightarrow} \text{Iso}$$

Mw = 4600

The mixing method was the same as that employed in Example 11. The phase transition behavior and response time of the obtained liquid-crystalline composition were as follows.

Phase transition behavior $$\text{glass} \underset{-30^\circ C}{\longleftrightarrow} S_C^* \underset{88^\circ C}{\longleftrightarrow} \text{Iso}$$

Response time at 25° C: 0.62 ms

The methods for measuring phase transition behavior and response time were the same as those used in Example 11, with the proviso that the orientation temperature was 86° C.

In the liquid crystal state of the composition, there was not observed the island structure peculiar to dispersion systems but was observed uniform liquid crystal phases whereby the compatibility of the high polymer with the other liquid crystal was confirmed.

What is claimed is:

1. A novel high polymer comprising the repeating unit (I) represented by the following formula $$\text{(I)} \quad \{\!\!-\!(CH_2)_m\!-\!\underset{CH_3}{\overset{CH_3}{Si}}\!-\!(CH_2)_n\!-\!Y\!-\!\underset{CH_3}{\overset{CH_3}{Si}}\!-\!\}$$

with $(OSi)_p-(CH_2)_a-O-\text{Ar}-COO-$ pendant group and CH₃ substituent wherein each of m and n is an integer of 2 to 5, p is an integer of 1 or 2, a is an integer of 4 to 20, b is an integer of 0 to 3, c is an integer of 1 to 7, * represents an asymmetric carbon atom, and Y is $$-(SiO)_k- \quad \text{or} \quad -Si-(CH_2)_j-,$$

(each with CH₃ substituents)

k being a number of 1 to 13 and j is an integer of 1 to 4.

2. The novel high polymer of claim 1 which forms chiral smectic C phase.

3. The novel high polymer of claim 1, wherein m is an integer of 3, n is an integer of 3, Y is $$-(SiO)_k- \quad \text{or} \quad -Si-(CH_2)_j-,$$

(each with CH₃ substituents)

k being a number of 1 to 5, j being an integer of 2, a an integer of 8 to 11, b is an integer of 0 and c is an integer of 2 to 5.

4. The novel high polymer of claim 3 comprising the following repeating unit $$\{\!\!-\!(CH_2)_3\!-\!Si\!-\!(CH_2)_3\!-\!SiO\!-\!Si\!-\!\}$$

with $OSi-(CH_2)_{10}-O-\text{Ar}-COO-\text{Ar}-\text{Ar}-COOCHC_3H_7^*$ pendant and CH₃ substituents.

5. The novel high polymer of claim 3 comprising the following repeating unit

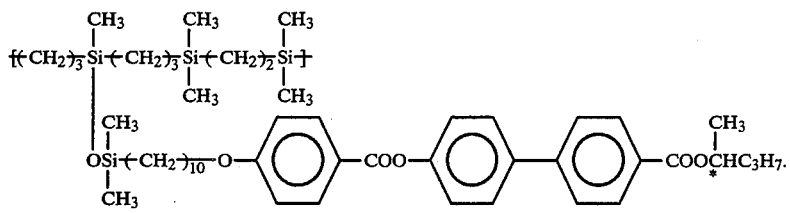

6. The novel high polymer of claim 3 comprising the following repeating unit

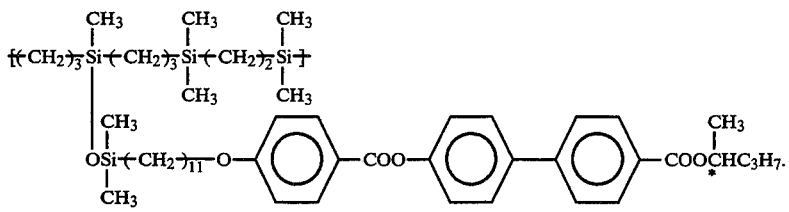

7. A diene compound having a structure represented by the following formula (II)

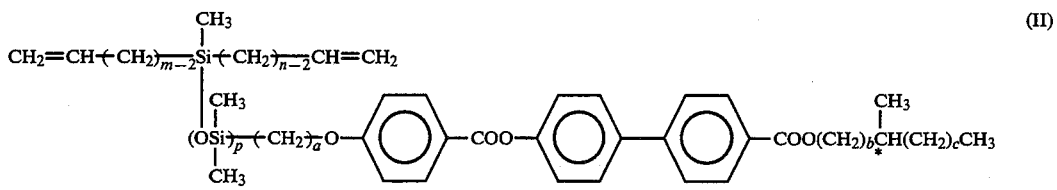

wherein each of m and n is an integer of 2 to 5, p is an integer of 1 or 2, a is an integer of 4 to 20, b is an integer of 0 to 3, c is an integer of 1 to 7 and * represents an asymmetric carbon atom.

8. The diene compound of claim 7, wherein m is an integer of 3, n is an integer of 3, a is an integer of 8 to 11, b is an integer of 0 and c is an integer of 2 to 5.

9. The diene compound of claim 8 having a structure represented by the following formula

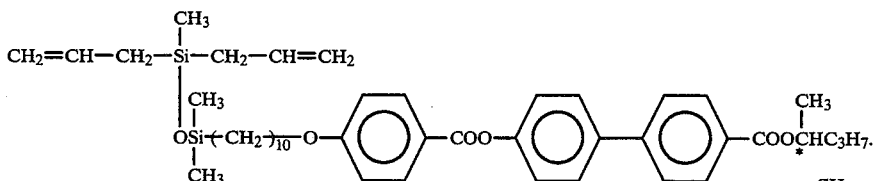

10. The diene compound of claim 8 having a structure represented by the following formula

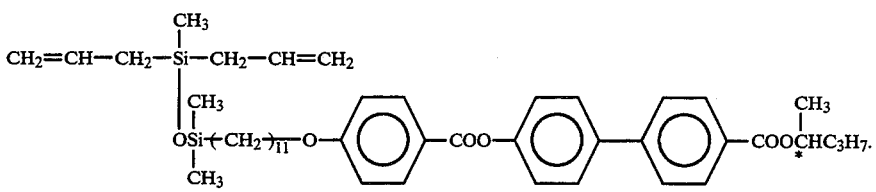

11. A ferroelectric liquid-crystalline composition comprising the novel high polymer of claim 1 and a low molecular weight smectic liquid-crystalline compound.

12. The ferroelectric liquid-crystalline composition of claim 11, wherein the ferroelectric liquid-crystalline composition contains 5 to 99% by weight of the novel high polymer based on the total of the novel high polymer and the low molecular weight smectic liquid-crystalline compound.

13. The ferroelectric liquid-crystalline composition of claim 11, wherein the low molecular weight smectic liquid-crystalline compound is a ferroelectric liquid-crystalline compound.

14. The ferroelectric liquid-crystalline composition of claim 11, wherein m is an integer of 3, n is an integer of 3, Y is

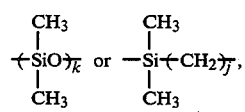

k being a number of 1 to 5, j being an integer of 2, a is an integer of 8 to 11, b is an integer of 0 and c is an integer of 2 to 5.

15. The ferroelectric liquid-crystalline composition of claim 14, wherein the novel high polymer has a repeating unit represented by the following formula

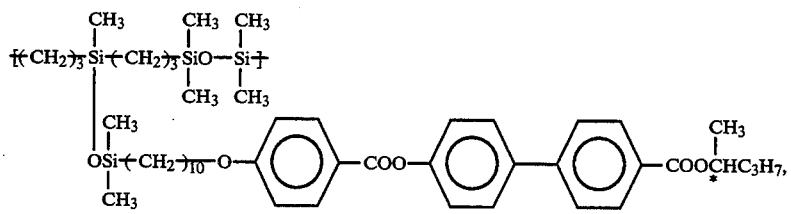

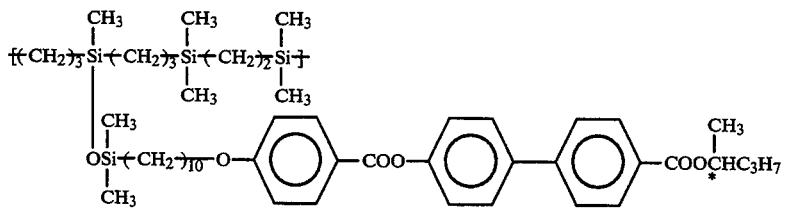

or

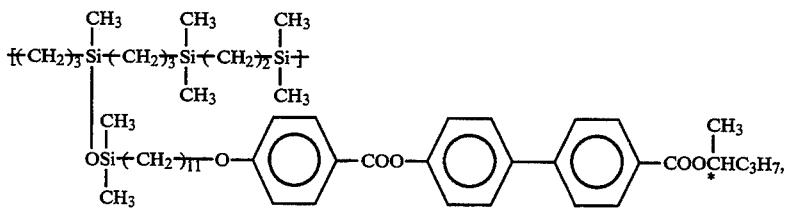

and the low molecular weight smectic liquid-crystalline compound has a structure represented by the following formula

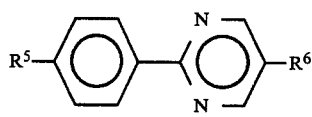

wherein $R^5$ is an alkyl group of 7 to 12 carbon atoms, an alkoxy group of 6 to 15 carbon atoms or an alkoxycarbonyl or acyloxy group of 6 to 12 carbon atoms, the alkyl group, the alkoxy group, the alkoxycarbonyl group and the acyloxy group laving a methylene group a portion of which is substituted or is not substituted by an ester bond or an oxygen atom, and $R^6$ is an alkyl group of 7 to 12 carbon atoms or an alkoxy group of 6 to 11 carbon atoms.

16. A ferroelectric liquid-crystalline composition comprising the novel high polymer of claim 1, a high polymer having the repeating unit (III) represented by the following formula

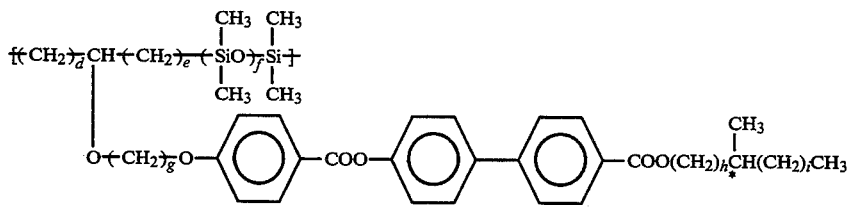

(III)

wherein each of d and e is an integer of 2 to 5, f is a number of 1 to 6, g is an integer of 8 to 12, h is an integer of 0 to 3, i is an integer of 1 to 7, and * represents an asymmetric carbon atom, and a low molecular weight smectic liquid-crystalline compound.

17. The ferroelectric liquid-crystalline composition of claim 16, wherein the amount of the total of the novel high polymer and the high polymer having the repeating unit (III) is 5 to 99% by weight based on the total of the novel high polymer, the high polymer having the repeating unit (III) and the low molecular weight smectic liquid-crystalline compound, and the amount of the novel high polymer is 40 to 99% by weight based on the total of the novel high polymer and the high polymer having the repeating unit (III).

18. The ferroelectric liquid-crystalline composition of claim 17, wherein m is an integer of 3, n is an integer of 3, Y is

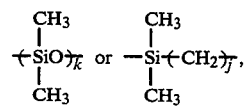

k being a number of 1 to 5, j being an integer of 2, a is an integer of 8 to 11, b is an integer of 0 and c is an integer of 2 to 5.

* * * * *